(12) United States Patent
Guzi et al.

(10) Patent No.: US 7,563,798 B2
(45) Date of Patent: *Jul. 21, 2009

(54) SUBSTITUTED PYRAZOLO[1,5-A]PYRIMIDINES AS PROTEIN KINASE INHIBITORS

(75) Inventors: Timothy J. Guzi, Chatham, NJ (US); Kamil Paruch, Garwood, NJ (US); Michael P. Dwyer, Scotch Plains, NJ (US); M. Arshad Siddiqui, Newton, MA (US); Panduranga Adulla P. Reddy, Walpole, MA (US); David B. Belanger, Cambridge, MA (US); Blake Hamann, Cambridge, MA (US); Patrick J. Curran, Winthrop, MA (US)

(73) Assignee: Schering Corporation, Kenilworth, NJ (US)

( * ) Notice: Subject to any disclaimer, the term of this patent is extended or adjusted under 35 U.S.C. 154(b) by 219 days.

This patent is subject to a terminal disclaimer.

(21) Appl. No.: 11/543,182

(22) Filed: Oct. 4, 2006

(65) Prior Publication Data

US 2007/0072882 A1 Mar. 29, 2007

Related U.S. Application Data

(63) Continuation-in-part of application No. 11/244,776, filed on Oct. 6, 2005, now Pat. No. 7,196,092, which is a continuation-in-part of application No. 10/654,157, filed on Sep. 3, 2003, now Pat. No. 7,078,525.

(60) Provisional application No. 60/408,030, filed on Sep. 4, 2002.

(51) Int. Cl.
*A61K 31/519* (2006.01)
*C07D 487/04* (2006.01)
*A61P 35/04* (2006.01)

(52) U.S. Cl. .................................. 514/259.3; 544/281
(58) Field of Classification Search ................ 544/281; 514/259.3
See application file for complete search history.

(56) References Cited

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Vippagunta et. al., Advanced Drug Delivery, 2001,, 48, 3-26.*

* cited by examiner

*Primary Examiner*—Brenda L Coleman
*Assistant Examiner*—Susanna Moore
(74) *Attorney, Agent, or Firm*—Palaiyur S. Kalyanaraman

(57) ABSTRACT

In its many embodiments, the present invention provides a class of pyrazolo [1,5-a]pyrimidine compounds as inhibitors of cyclin dependent kinases (CDKs), methods of preparing such compounds, pharmaceutical compositions containing one or more such compounds, methods of preparing pharmaceutical formulations comprising one or more such compounds, and methods of treatment, prevention, inhibition, or amelioration of one or more diseases associated with the CDKs using such compounds or pharmaceutical compositions. An illustrative compound of the invention is shown below:

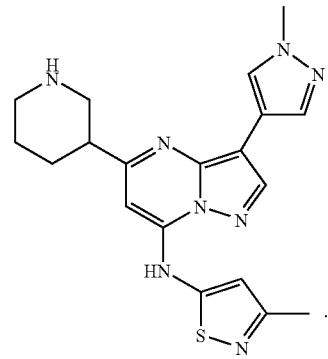

3 Claims, No Drawings

SUBSTITUTED PYRAZOLO[1,5-A]PYRIMIDINES AS PROTEIN KINASE INHIBITORS

REFERENCE TO PRIORITY APPLICATIONS

This application is a Continuation-in-Part of U.S. application Ser. No. 11/244,776 filed Oct. 6, 2005 (which published as US 2006/0040958 on Feb. 23, 2006), which is a Continuation-in-Part of U.S. application Ser. No. 10/654,157 filed Sep. 3, 2003 (which published as US 2004/0102451), which claims the benefit of priority from U.S. Provisional Patent Application Ser. No. 60/408,030, filed on Sep. 4, 2002.

FIELD OF THE INVENTION

The present invention relates to pyrazolo[1,5-a]pyrimidine compounds useful as protein kinase inhibitors, pharmaceutical compositions containing the compounds, and methods of treatment using the compounds and compositions to treat diseases such as, for example, cancer, inflammation, arthritis, viral diseases, neurodegenerative diseases such as Alzheimer's disease, cardiovascular diseases, and fungal diseases.

BACKGROUND OF THE INVENTION

The cyclin-dependent kinases (CDKs) are serine/threonine protein kinases, which are the driving force behind the cell cycle and cell proliferation. Individual CDK's, such as, CDK1, CDK2, CDK3, CDK4, CDK5, CDK6 and CDK7, CDK8 and the like, perform distinct roles in cell cycle progression and can be classified as either G1, S, or G2M phase enzymes. Uncontrolled proliferation is a hallmark of cancer cells, and misregulation of CDK function occurs with high frequency in many important solid tumors. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over—or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development years, a number of adenosine 5'-triphosphate (ATP) competitive small organic molecules as well as peptides have been reported in the literature as CDK inhibitors for the potential treatment of cancers. U.S. Pat. No. 6,413,974, col. 1, line 23- col. 15, line 10 offers a good description of the various CDKs and their relationship to various types of cancer.

CDK inhibitors are known. For example, flavopiridol (Formula I) is a nonselective CDK inhibitor that is currently undergoing human clinical trials, A. M. Sanderowicz et al, *J. Clin. Oncol.* (1998) 16, 2986-2999.

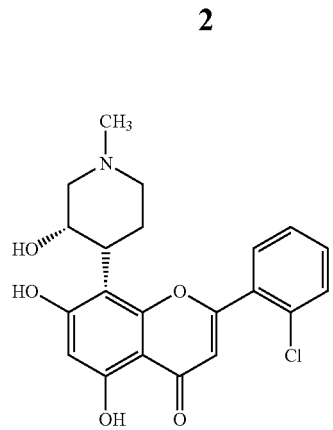

Formula I

Other known inhibitors of the CDKs include, for example, olomoucine (J. Vesely et al, *Eur. J. Biochem.*, (1994) 224, 771-786) and roscovitine (I. Meijer et al, *Eur. J. Biochem.*, (1997) 243, 527-536). U.S. Pat. No. 6,107,305 describes certain pyrazolo[3,4-b] pyridine compounds as CDK inhibitors. An illustrative compound from the '305 patent has the Formula II:

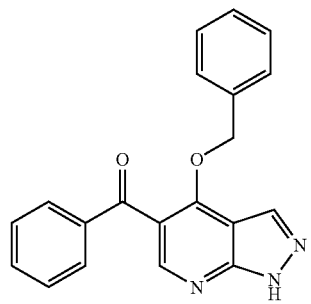

Formula II

K. S. Kim et al, *J. Med. Chem.* 45 (2002) 3905-3927 and WO 02/10162 disclose certain aminothiazole compounds as CDK inhibitors.

Pyrazolopyrimidines are known. For Example, W092/18504, W002/50079, W095/35298, W002/40485, EP94304104.6, EP0628559 (equivalent to U.S. Pat. Nos. 5,602,136, 5,602,137 and 5,571,813), U.S. Pat. No. 6,383,790, *Chem. Pharm. Bull.*, (1999) 47 928, *J. Med. Chem.*, (1977) 20, 296, *J. Med. Chem.*, (1976) 19 517 and *Chem. Pharm. Bull.*, (1962) 10 620 disclose various pyrazolopyrimidines. The string of parent cases for this present application, U.S. application Ser. No. 11/244,776 filed Oct. 6, 2005 (which published as US 2006/0040958 on Feb. 23, 2006), and U.S. application Ser. No. 10/654,157 filed Sep. 3, 2003 (which published as US 2004/0102451) should be considered as part of this invention.

There is a need for new compounds, formulations, treatments and therapies to treat diseases and disorders associated with CDKs. It is, therefore, an object of this invention to provide compounds useful in the treatment or prevention or amelioration of such diseases and disorders.

SUMMARY OF THE INVENTION

In its many embodiments, the afore-mentioned U.S. application Ser. No. 11/244,776 provides a novel class of pyrazolo[1,5-a]pyrimidine compounds as inhibitors of cyclin dependent kinases, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the CDKs using such compounds or pharmaceutical compositions.

In one aspect, U.S. application Ser. No. 11/244,776 discloses a compound, or pharmaceutically acceptable salts, solvates, esters or prodrugs of said compound, said compound having the general structure shown in Formula III:

Formula III

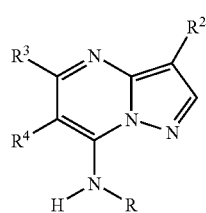

wherein:

R is heteroaryl, wherein said heteroaryl can be unsubstituted or optionally independently substituted with one or more moieties which can be the same or different, each moiety being independently selected from the group consisting of halogen, alkyl, aryl, cycloalkyl, $CF_3$, $OCF_3$, CN, —$OR^5$, —$NR^5R^6$, —$C(R^4R^5)_nOR^5$, —$C(O_2)R^5$, —$C(O)R^5$, —$C(O)NR^5R^6$, —$SR^6$, —$S(O_2)R^7$, —$S(O_2)NR^5R^6$, —$N(R^5)S(O_2)R^7$, —$N(R^5)C(O)R^7$ and —$N(R^5)C(O)NR^5R^6$;

$R^2$ is selected from the group consisting of $R^9$, alkyl, alkynyl, aryl, heteroaryl, $CF_3$, heterocyclylalkyl, alkynylalkyl, cycloalkyl, —$C(O)OR^4$, alkyl substituted with 1-6 $R^9$ groups which can be the same or different and are independently selected from the list of $R^9$ shown later below,

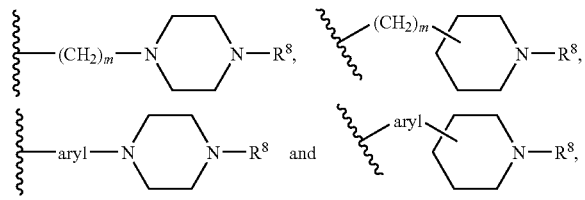

wherein the aryl in the above-noted definitions for $R^2$ can be unsubstituted or optionally substituted with one or more moieties which can be the same or different, each moiety being independently selected from the group consisting of halogen, CN, —$OR^5$, $SR^5$, —$CH_2OR^5$, —$C(O)R^5$, —$SO_3H$, —$S(O_2)R^6$, —$S(O_2)NR^5R^6$, —$NR^5R^6$, —$C(O)NR^5R^6$, —$CF_3$, and —$OCF_3$;

$R^3$ is selected from the group consisting of H, halogen, —$NR^5R^6$, —$C(O)OR^4$, —$C(O)NR^5R^6$, alkyl, alkynyl, cycloalkyl, cycloalkylalkyl, aryl, arylalkyl, heterocyclyl, heterocyclylalkyl, heteroaryl,

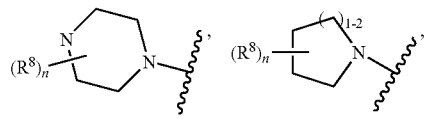

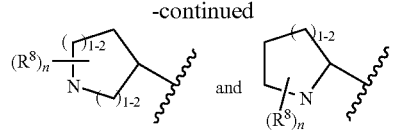

wherein each of said alkyl, cycloalkyl, aryl, arylalkyl, heterocyclyl, heterocyclylalkyl, heteroaryl and heteroarylalkyl for $R^3$ and the heterocyclyl moieties whose structures are shown immediately above for $R^3$ can be substituted or optionally independently substituted with one or more moieties which can be the same or different, each moiety being independently selected from the group consisting of halogen, alkyl, aryl, cycloalkyl, $CF_3$, CN, —$OCF_3$, —$(CR^4R^5)_nOR^5$, —$OR^5$, —$NR^5R^6$, —$(CR^4R^5)_nNR^5R^6$, —$C(O_2)R^5$, —$C(O)R^5$, —$C(O)NR^5R^6$, —$SR^6$, —$S(O_2)R^6$, —$S(O_2)NR^5R^6$, —$N(R^5)S(O_2)R^7$, —$N(R^5)C(O)R^7$ and —$N(R^5)C(O)NR^5R^6$;

$R^4$ is H, halo or alkyl;

$R^5$ is H or alkyl;

$R^6$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, $CF_3$, $OCF_3$, CN, —$OR^5$, —$NR^5R^{10}$, —$N(R^5)Boc$, —$(CR^4R^5)_nOR^5$, —$C(O_2)R^5$, —$C(O)R^5$, —$C(O)NR^5R^{10}$, —$SO_3H$, —$SR^{10}$, —$S(O_2)R^7$, —$S(O_2)NR^5R^{10}$, —$N(R^5)S(O_2)R^7$, —$N(R^5)C(O)R^7$ and —$N(R^5)C(O)NR^5R^{10}$;

$R^{10}$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, $CF_3$, $OCF_3$, CN, —$OR^5$, —$NR^4R^5$, —$N(R^5)Boc$, —$(CR^4R^5)_nOR^5$, —$C(O_2)R^5$, —$C(O)NR^4R^5$, —$C(O)R^5$, —$SO_3H$, —$SR^5$, —$S(O_2)R^7$, —$S(O_2)NR^4R^5$, —$N(R^5)S(O_2)R^7$, —$N(R^5)C(O)R^7$ and —$N(R^5)C(O)NR^4R^5$;

or optionally (i) $R^5$ and $R^{10}$ in the moiety —$NR^5R^{10}$, or (ii) $R^5$ and $R^6$ in the moiety —$NR^5R^6$, may be joined together to form a cycloalkyl or heterocyclyl moiety, with each of said cycloalkyl or heterocyclyl moiety being unsubstituted or optionally independently being substituted with one or more $R^9$ groups;

$R^7$ is selected from the group consisting of alkyl, cycloalkyl, aryl, heteroaryl, arylalkyl and heteroarylalkyl, wherein each of said alkyl, cycloalkyl, heteroarylalkyl, aryl, heteroaryl and arylalkyl for $R^7$ can be unsubstituted or optionally independently substituted with one or more moieties which can be the same or different, each moiety being independently selected from the group consisting of halogen, alkyl, aryl, cycloalkyl, $CF_3$, $OCF_3$, CN, —$OR^5$, —$NR^5R^{10}$, —$CH_2OR^5$, —$C(O_2)R^5$, —$C(O)NR^5R^{10}$, —$C(O)R^5$, —$SR^{10}$, —$S(O_2)R^{10}$, —$S(O_2)NR^5R^{10}$, —$N(R^5)S(O_2)R^{10}$, —$N(R^5)C(O)R^{10}$ and —$N(R^5)C(O)NR^5R^{10}$;

$R^8$ is selected from the group consisting of $R^6$, —$C(O)NR^5R^{10}$, —$CH_2OR^4$, —$C(O)OR^6$, —$C(O)R^7$ and —$S(O_2)R^7$;

$R^9$ is selected from the group consisting of halogen, —CN, —NR$^5$R$^6$, —(CH$_2$)$_n$OR$^4$, —C(O$_2$)R$^6$, —C(O)NR$^5$R$^6$, —OR$^6$, —SR$^6$, —S(O$_2$)R$^7$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$;

m is 0 to 4; and n is 1 to 4.

The present invention discloses the compounds shown in Table 1, or a pharmaceutically acceptable salt, solvate, ester or prodrug thereof.

The compounds of the present invention can be useful as protein kinase inhibitors and can be useful in the treatment and prevention of proliferative diseases, for example, cancer, inflammation and arthritis. They may also be useful in the treatment of neurodegenerative diseases such Alzheimer's disease, cardiovascular diseases, viral diseases and fungal diseases.

DETAILED DESCRIPTION

In one embodiment, the present invention discloses pyrazolo[1,5-a]pyrimidine compounds, or a pharmaceutically acceptable salt, solvate, ester or prodrug thereof.

In another embodiment, this invention discloses the inventive compounds shown in Table 1 as well as a pharmaceutically acceptable salt, solvate, ester or prodrug thereof.

TABLE 1

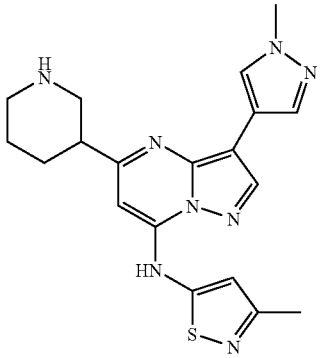

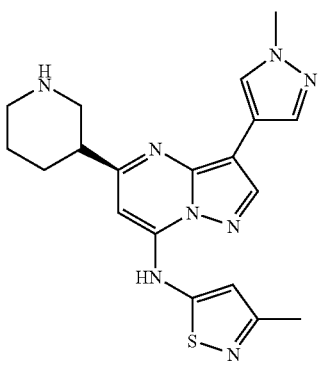

TABLE 1-continued

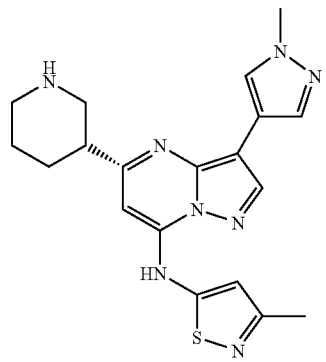

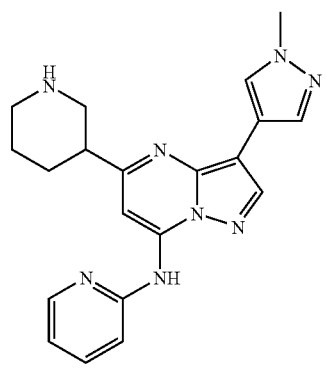

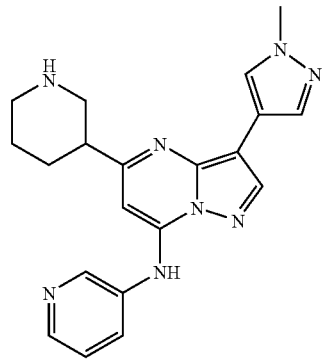

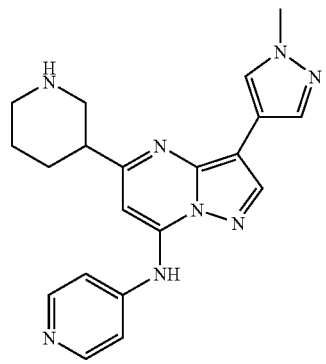

TABLE 1-continued
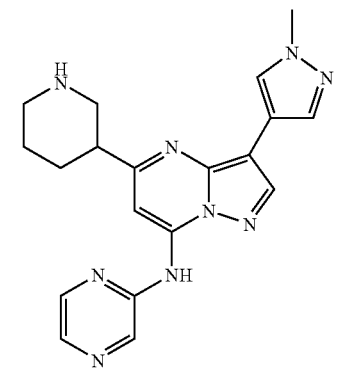
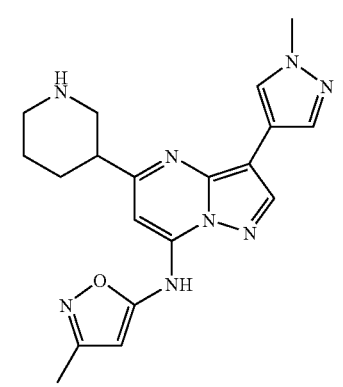
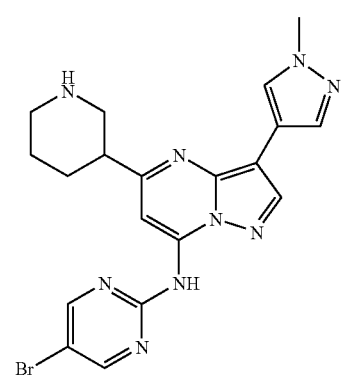
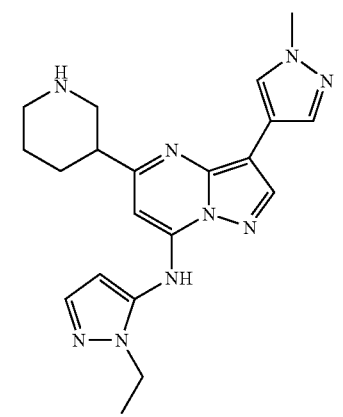
TABLE 1-continued
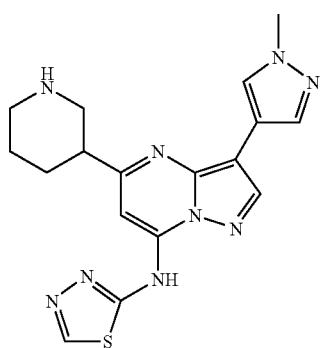
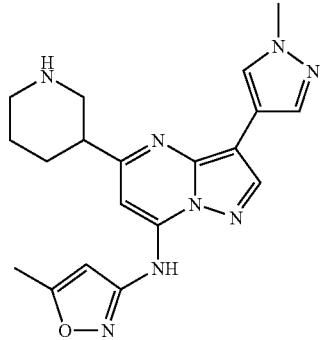
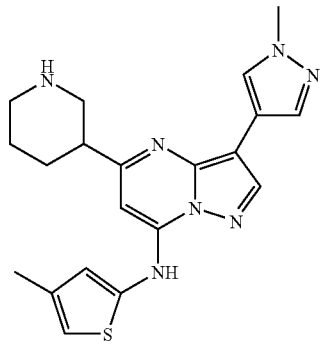
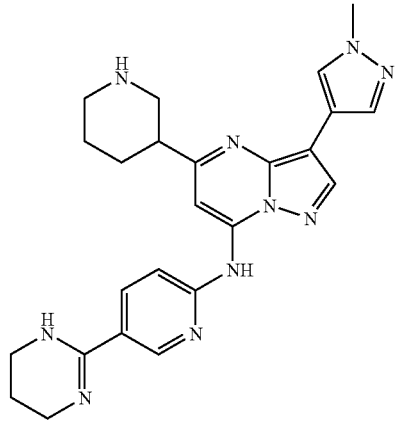

TABLE 1-continued
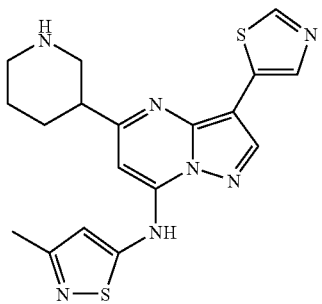
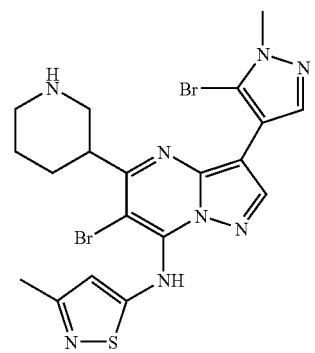
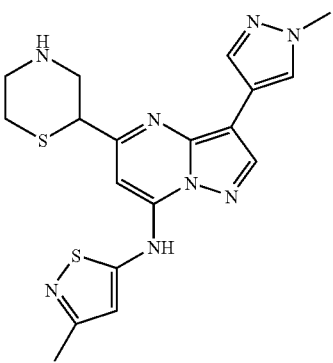
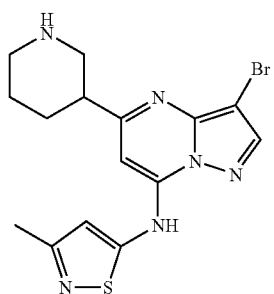
TABLE 1-continued
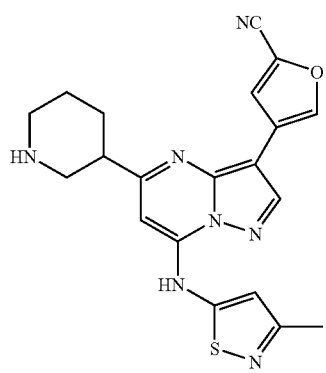
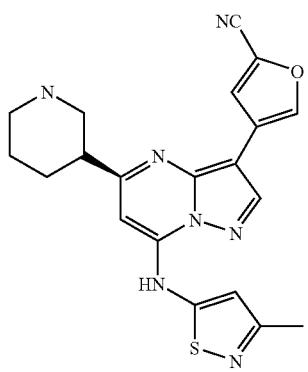
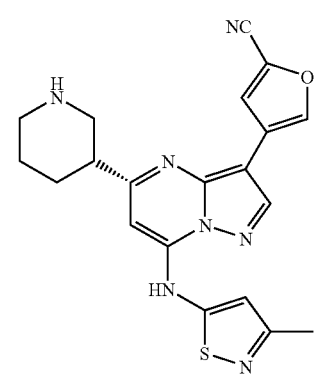
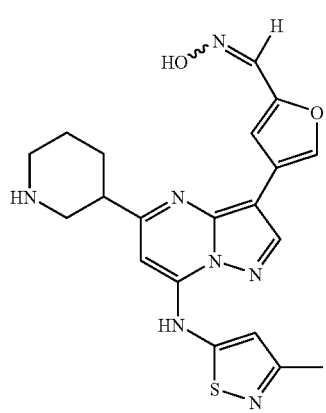

TABLE 1-continued
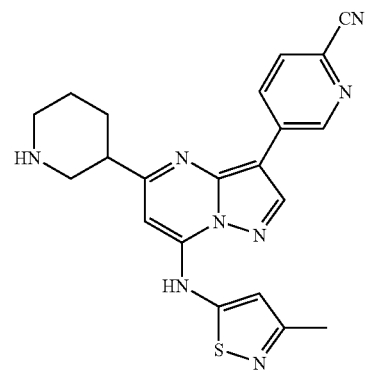
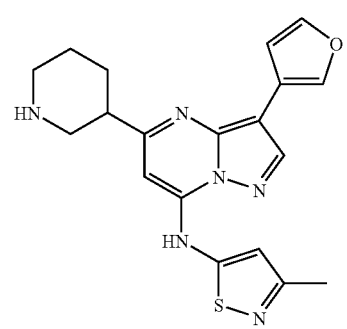
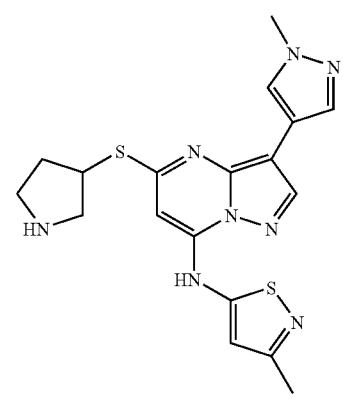
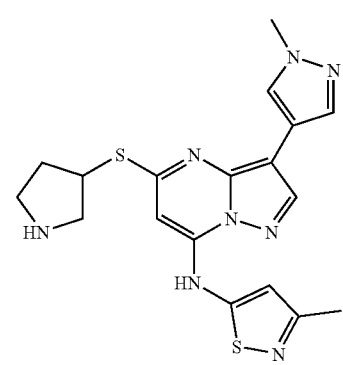
TABLE 1-continued
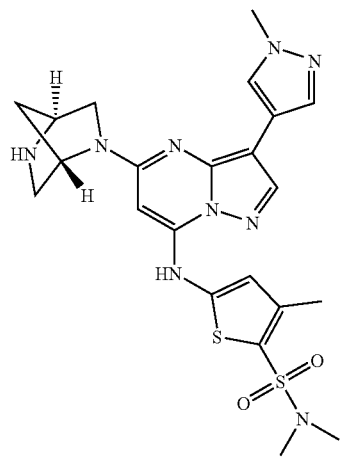
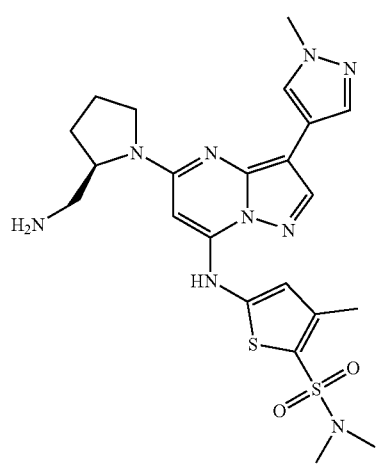
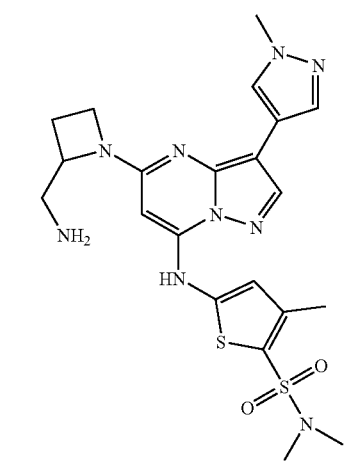

TABLE 1-continued
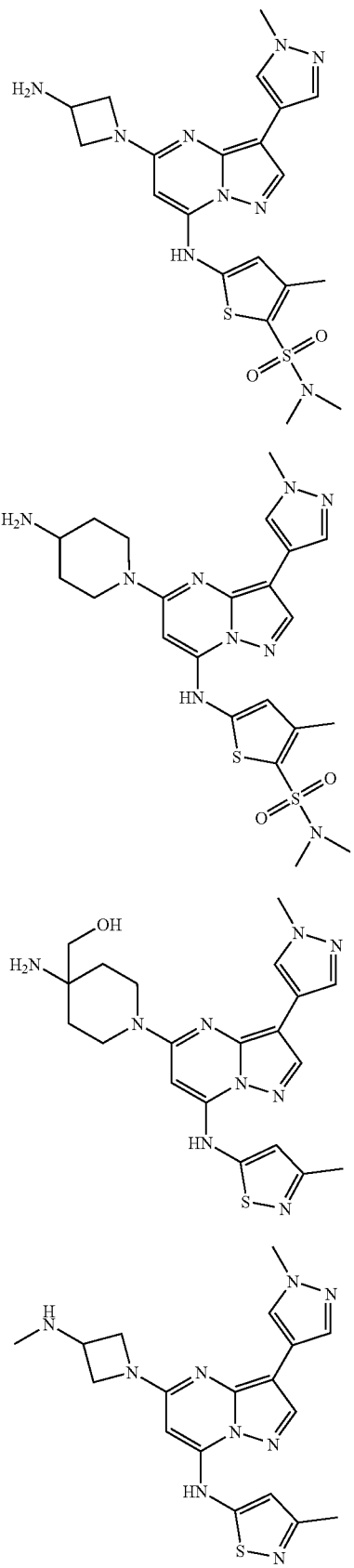
TABLE 1-continued
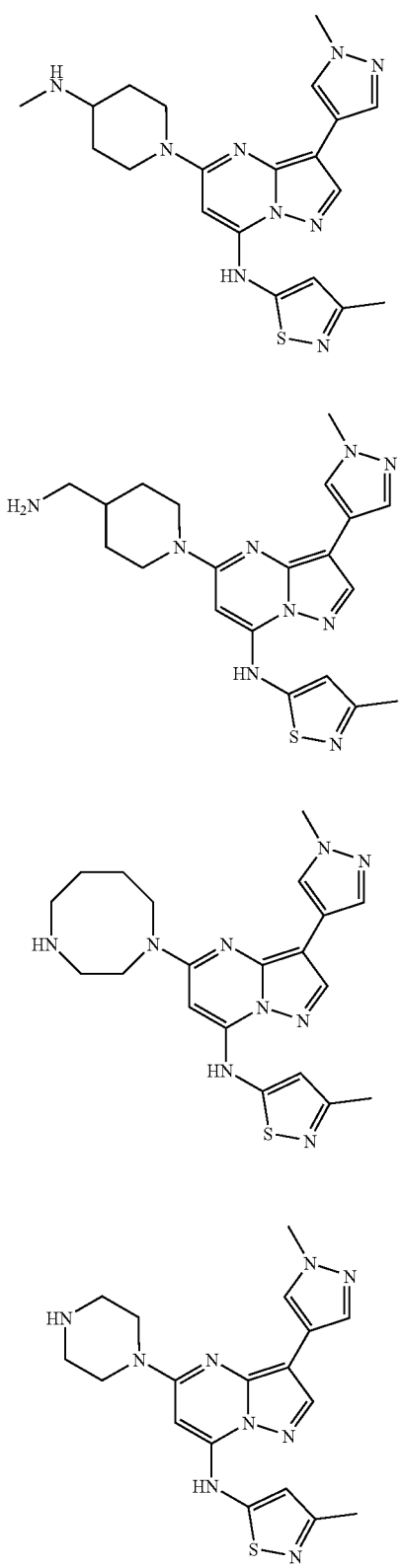

TABLE 1-continued
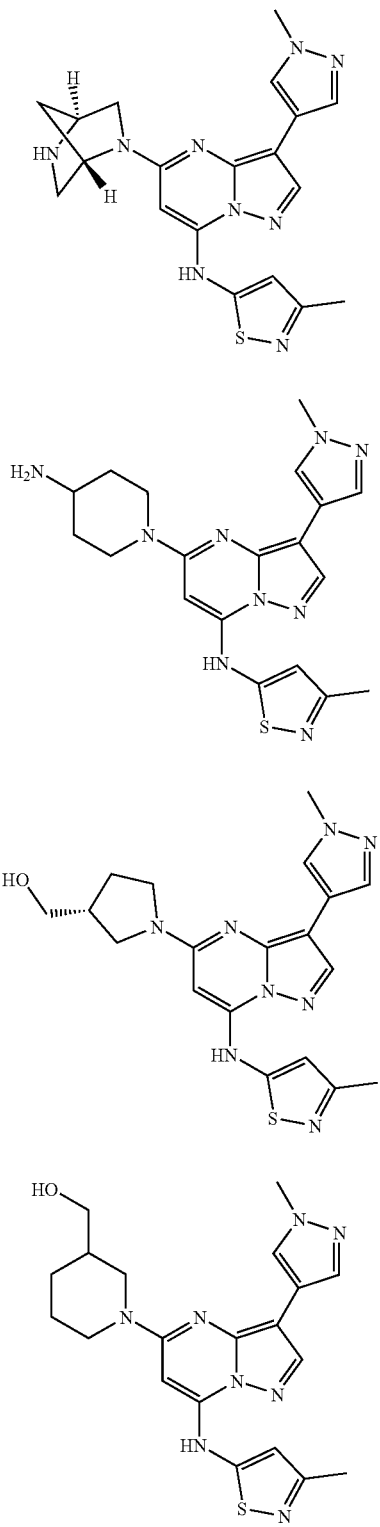
TABLE 1-continued
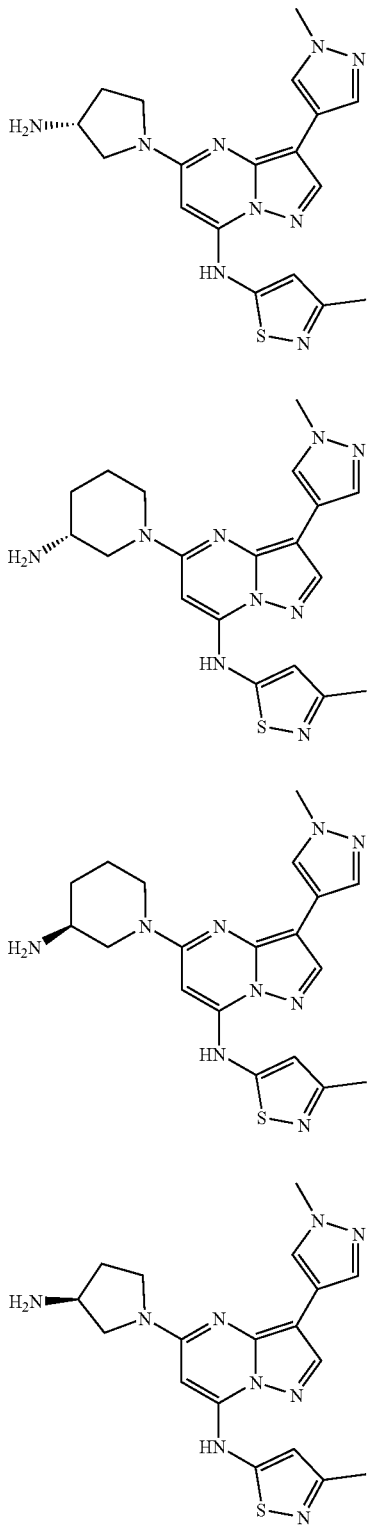

TABLE 1-continued

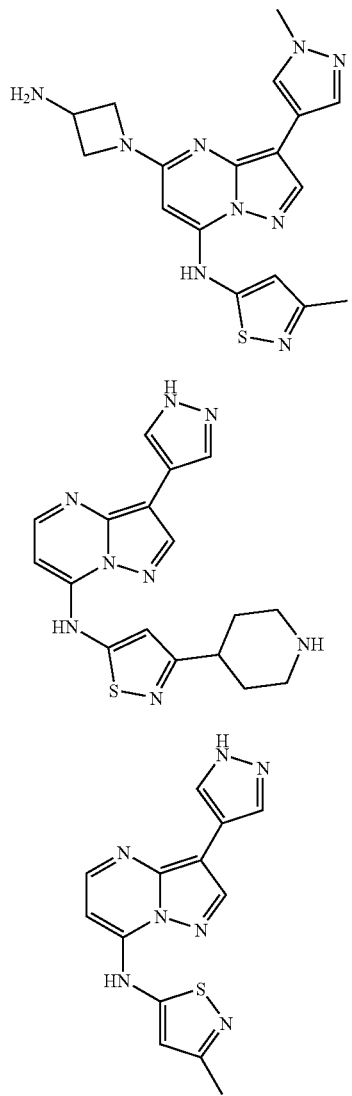

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g. =N—OH), —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), oxime (e.g.=N—OH), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

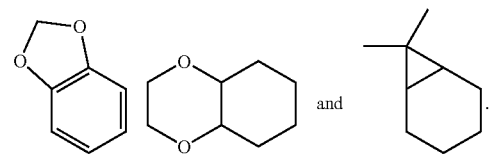

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, dihydroimidazole, dihydrooxazole, dihydrooxadiazole, dihydrothiazole, 3,4-dihydro-2H-pyran, dihydrofuranyl, fluorodihydrofuranyl, 7-oxabicyclo[2.2.1]heptenyl, dihydrothiophenyl, dihydrothiopyranyl, and the like.

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, 0 or S, as well as there are no N or S groups on carbon adjacent to another heteroatom. Thus, for example, in the ring:

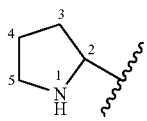

there is no —OH attached directly to carbons marked 2 and 5.

It should also be noted that tautomeric forms such as, for example, the moieties:

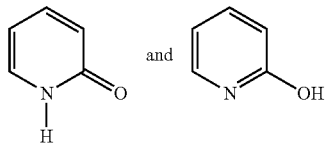

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of The invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-(C1-C2)alkyl and piperidino-, pyrrolidino- or morpholino$(C_2-C_3)$alkyl, and the like.

Similarly, if a compound of The invention contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, $-P(O)(O(C_1-C_6)$alkyl$)_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, $-C(OH)C(O)OY^1$ wherein $Y^1$ is H, $(C_1-C_6)$alkyl or benzyl, $-C(OY^2)Y^3$ wherein $Y^2$ is $(C_1-C_4)$ alkyl and $Y^3$ is $(C_1-C_6)$alkyl, carboxy $(C_1-C_6)$alkyl, amino$(C_1-C_4)$alkyl or mono-N— or di-N,N-$(C_1-C_6)$alkylaminoalkyl, $-C(Y^4)Y^5$ wherein $Y^4$ is H or methyl and $Y^5$ is mono-N— or di-N,N-$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example 1. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of the invention can form salts which are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of The invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

The compounds of the invention, and salts, solvates, esters and prodrugs thereof, may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of The invention incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated, for example, by use of chiral HPLC column.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, 35S, $^{18}F$, and $^{36}Cl$, respectively.

Certain isotopically-labelled compounds of the invention (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of The invention can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of the invention, and of the salts, solvates, esters and prodrugs of the compounds of the invention, are intended to be included in the present invention.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The compounds according to the invention have pharmacological properties; in particular, the compounds of the invention can be inhibitors of protein kinases such as, for example, the inhibitors of the cyclin-dependent kinases, mitogen-activated protein kinase (MAPK/ERK), glycogen synthase kinase 3(GSK3beta) and the like. The cyclin dependent kinases (CDKs) include, for example, CDC2 (CDK1), CDK2, CDK4, CDK5, CDK6, CDK7 CDK8 and CDK9. The novel compounds of the invention are expected to be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974 cited earlier, the disclosure of which is incorporated herein.

More specifically, the compounds of the invention can be useful in the treatment of a variety of cancers, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of CDKs in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of the invention may also be useful in the treatment of Alzheimer's disease, as suggested by the recent finding that CDK5 is involved in the phosphorylation of tau protein (*J. Biochem*, (1995) 117, 741-749).

Compounds of the invention may induce or inhibit apoptosis. The apoptotic response is aberrant in a variety of human diseases. Compounds of The invention, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of the invention, as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of the invention may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of the invention may also be useful in inhibiting tumor angiogenesis and metastasis.

Compounds of the invention may also act as inhibitors of other protein kinases, e.g., protein kinase C, her2, raf 1, MEK1, MAP kinase, EGF receptor, PDGF receptor, IGF receptor, P13 kinase, weel kinase, Src, Abl and thus be effective in the treatment of diseases associated with other protein kinases.

Another aspect of this invention is a method of treating a mammal (e.g., human) having a disease or condition associated with the CDKs by administering a therapeutically effective amount of at least one compound of The invention, or a pharmaceutically acceptable salt or solvate of said compound to the mammal.

A preferred dosage is about 0.001 to 500 mg/kg of body weight/day of the compound of the invention. An especially preferred dosage is about 0.01 to 25 mg/kg of body weight/day of a compound of the invention, or a pharmaceutically acceptable salt or solvate of said compound.

The compounds of this invention may also be useful in combination (administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™(4-[2-[4-[(11R)-3,10-dibromo-8-chloro-6,11-dihydro-5H-benzo[5,6]cyclohepta[1,2-b]pyridin-11-yl-]-1-piperidinyl]-2-oxoehtyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, Clofarabine (Clolar® from Genzyme Oncology, Cambridge, Massachusetts), cladribine (Leustat® from Janssen-Cilag Ltd.), aphidicolon, rituxan (from Genentech/Biogen Idec), sunitinib (Sutent® from Pfizer), dasatinib (or BMS-354825 from Bristol-Myers Squibb), tezacitabine (from Aventis Pharma), Sml1, fludarabine (from Trigan Oncology Associates), pentostatin (from BC Cancer Agency), triapine (from Vion Pharmaceuticals), didox (from Bioseeker Group), trimidox (from ALS Therapy Development Foundation), amidox, 3-AP (3-aminopyridine-2-carboxaldehyde thiosemicarbazone), MDL-101,731 ((E)-2'-deoxy-2'-(fluoromethylene)cytidine) and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaeuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225 (or Cetuximab from Merck KGaA, Darmstadt, Germany), and Campath.

The compounds of this invention may specifically be useful in combination (administered together, concurrently or sequentially) with temozolomide and/or radiation therapy.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. Compounds of The invention may also be administered sequentially with known anticancer or cytotoxic agents when a combination formulation is inappropriate. The invention is not limited in the sequence of administration; compounds of The invention may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in an aspect, this invention includes combinations comprising an amount of at least one compound of the invention, or a pharmaceutically acceptable salt, solvate, ester or prodrug thereof, and an amount of one or more anti-cancer treatments and anti-cancer agents listed above wherein the amounts of the compounds/treatments result in desired therapeutic effect.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of the invention, or a pharmaceutically acceptable salt, solvate, ester or prodrug of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of the invention, or a pharmaceutically acceptable salt, solvate, ester or prodrug of said compound and a pharmaceutically acceptable carrier, vehicle or diluent.

Yet another aspect of this invention is a kit comprising an amount of at least one compound of The invention, or a pharmaceutically acceptable salt, solvate, ester or prodrug of said compound and an amount of at least one anticancer therapy and/or anti-cancer agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

The following solvents and reagents may be referred to by their abbreviations in parenthesis:

Thin layer chromatography: TLC
dichloromethane: CH$_2$Cl$_2$
ethyl acetate: AcOEt or EtOAc
methanol: MeOH
trifluoroacetate: TFA
triethylamine: Et$_3$N or TEA
butoxycarbonyl: n-Boc or Boc
nuclear magnetic resonance spectroscopy: NMR
liquid chromatography mass spectrometry: LCMS
high resolution mass spectrometry: HRMS
milliliters: mL
millimoles: mmol
microliters: μl
grams: g
milligrams: mg
room temperature or rt (ambient): about 25° C.

EXAMPLES

Preparative Example 10-C

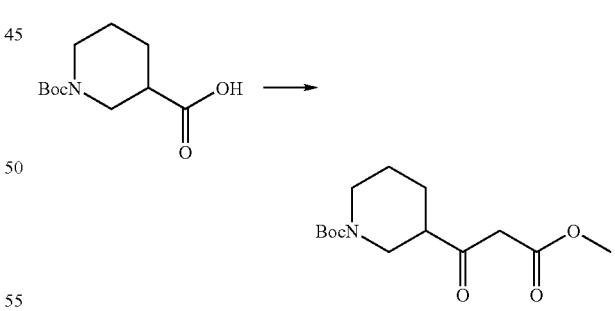

SOCl$_2$ (18.5 mL) was added slowly under N$_2$ to a stirred mixture of the acid (50.0 g, 218 mmol) and pyridine (44.0 mL) in anhydrous CH$_2$Cl$_2$ (60 mL). The mixture was stirred at 25° C. for 20 min, then Meldrum's acid (35.0 g, 243 mmol) and DMAP (66.6 g, 546 mmol) were added and the mixture was stirred under N$_2$ for 1 hr. Then Et$_2$O (2 L) was added, the mixture was washed with 1 M HCl (3×500 mL), brine (500 mL), and the organic layer was dried over Na$_2$SO$_4$, filtered, and the solvent was evaporated. The residue was dissolved in MeOH (580 mL), and the mixture was refluxed for 4 hr. The solvent was evaporated and the residue was purified by col- Preparative Example 20-C

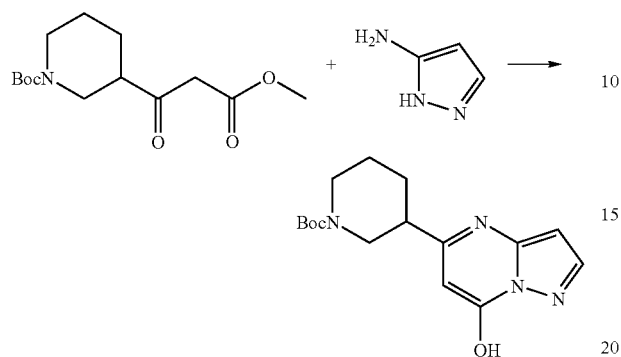

A mixture of the β-ketoester from Preparative Example 10-C (20.0 g, 70.1 mmol) and 3-aminopyrazole (5.40 g, 65.0 mmol) in anhydrous toluene (60 mL) was stirred and refluxed under $N_2$ for 24 hr. The solvent was evaporated and the residue was purified by column chromatography on silica gel with 20:1 $CH_2Cl_2$/MeOH as eluent. White solid (15.0 g, 73%) was obtained.

Preparative Example 30-C

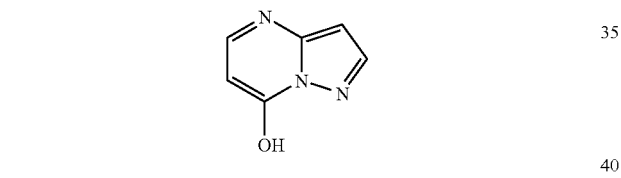

The known compound was prepared according to the procedure documented in *J. Heterocyclic Chem.* 1986, 23, 349.

Preparative Example 40-C

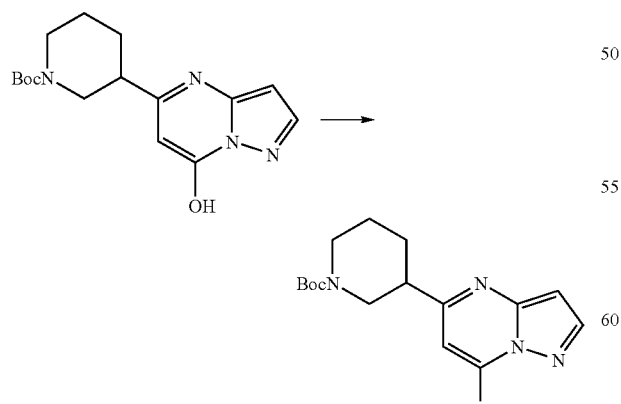

A mixture of the product from Preparative Example 20-C (12.50 g, 39.3 mmol), N,N-dimethylaniline (15.5 mL), and $POCl_3$ (125 mL) was stirred at 25° C. for 4 days. Excess of $POCl_3$ was evaporated and the residue was poured into saturated aqueous $NaHCO_3$ (600 mL). The mixture was extracted with $CH_2Cl_2$ (3×200 mL), the combined extracts were dried over $Na_2SO_4$, filtered, and the solvent was evaporated. The residue was purified by column chromatography on silica gel with 8:1 $CH_2Cl_2$/EtOAc as eluent. Pale yellow wax (9.41 g, 71%) was obtained.

Preparative Example 50-C

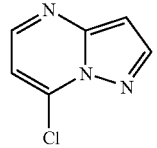

The known compound was prepared according to the procedure documented in *J. Med. Chem.* 1981, 24(5), 610-613.

Preparative Example 60-C

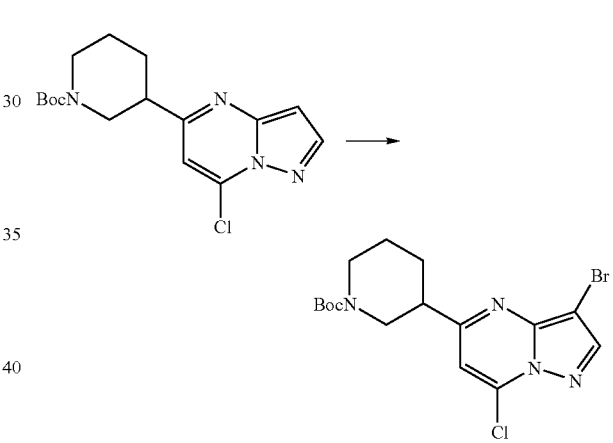

A solution of NBS (4.03 g, 22.7 mmol) in anhydrous $CH_3CN$ (40 mL) was added under $N_2$ to a stirred solution of the product from Preparative Example 40-C (7.63 g, 22.7 mmol) in anhydrous $CH_3CN$ (60 mL) and $CH_2Cl_2$ (20 mL). The mixture was stirred for 2 hr, the solvents were evaporated, and the residue was purified by column chromatography on silica gel with 20:1 $CH_2Cl_2$/EtOAc as eluent. Pale yellow solid foam (9.20 g, 97%) was obtained.

Preparative Example 70-C

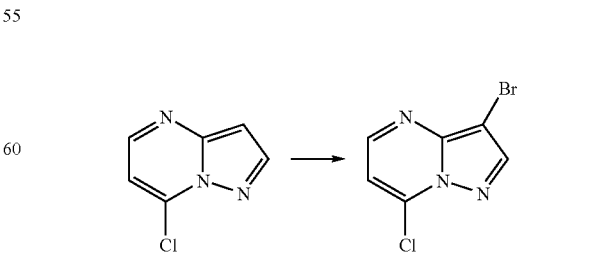

By essentially same procedure set forth in Preparative Example 60-C, the 7-chloro adduct (1.2 g, 7.5 mmol) from Preparative Example 50-C was treated with NBS (1.5 g, 8.2 mmol) to afford 1.2 g (69% yield) of a yellow solid. MS=233.9 [M+H].

Preparative Example 80-C

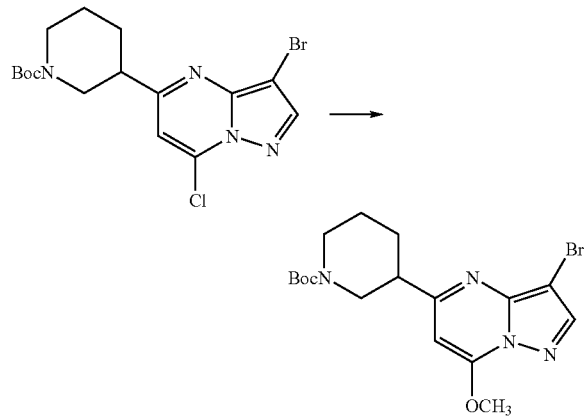

A mixture of the product from Preparative Example 60-C (8.00 g, 19.3 mmol) and NaOMe (2.16 g, 40.0 mmol) in anhydrous MeOH (100 mL) was stirred for 20 hr. CH$_2$Cl$_2$ (200 mL) was then added, the mixture was filtered through Celite, the solvent was evaporated, and the residue was purified by column chromatography on silica gel with 2:1 CH$_2$Cl$_2$/EtOAc as eluent. White solid (7.75 g, 98%) was obtained.

Preparative Example 90-C

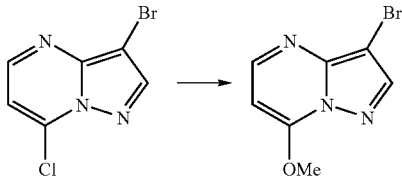

By essentially same procedure set forth in Preparative Example 80-C, the 7-chloro adduct (1.6 g, 6.9 mmol) from Preparative Example 70-C was treated with NaOMe (0.74 g, 13.8 mmol) to afford 1.5 g (95% yield) of a yellow/orange solid. LC-MS=228.1 [M+H]; 97% purity.

Preparative Example 100-C

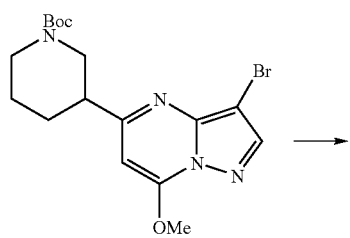

-continued

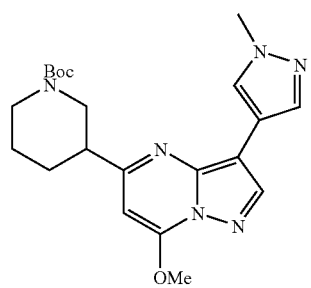

To a mixture of Boc derivative (3.0 g, 7.3 mmol) from Preparative Example 80-C in DME/H$_2$O (16 mL/4 mL) was added 1-methyl-4-(4,4,5,5-tetramethyl-1,3,2-dioxaborolan-2yl)-1H-pyrazole (2.8 g, 13.5 mmol) and Na$_2$CO$_3$ (3.9 g, 36.4 mmol). N$_2$ was bubbled thru the solution for 20 min with stirring whereupon PdCl$_2$(PPh$_3$)$_2$ (0.39 g, 0.47 mmol) was added. The mixture was heated to 110° C. and was stirred for 12 hr. The mixture was cooled to rt, concentrated under reduced pressure and placed under high vacuum. The crude product was purified by flash chromatography using a 30:1 mixture of CH$_2$Cl$_2$/MeOH as eluent to afford 1.57 g (52% yield) as an orange/brown solid. LC-MS:=413.2 [M+H] 97% purity.

Preparative Example 110-C

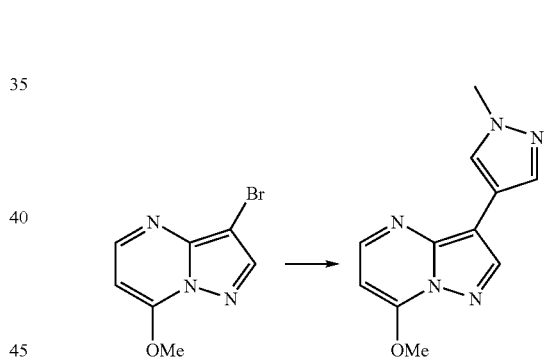

By essentially same procedure set forth in Preparative Example 100-C, the 7-methoxy adduct (0.80 g, 3.5 mmol) from Preparative Example 90-C was converted to 0.68 g (84% yield) of an orange solid. MS=230.2. [M+H].

Preparative Example 120-C

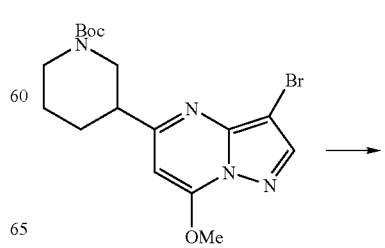

-continued

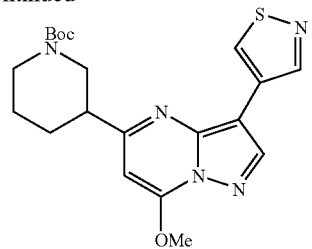

To a solution of 3-Br adduct (0.27 g, 0.67 mmol) from Preparative Example 80-C in CH$_3$CN (4 mL) at rt was 4-tributylstannylthiazole (0.50 g, 1.34 mmol) followed by PdCl$_2$(PPh$_3$)$_2$ (47 mg, 0.067 mmol). The resulting mixture was degassed under aspirator vacuum and filled with N$_2$ six times. The mixture was fitted with a condenser and was heated to 85° C. The mixture was stirred for 12 hr, cooled to rt, and diluted with EtOAc (10 mL). The mixture was filtered thru a Celite pad which was washed with EtOAc (3×5 mL), CH$_2$Cl$_2$ (1×5 mL) and MeOH (1×5 mL). The resulting filtrate was concentrated under reduced pressure and was placed under high vacuum. The crude product was purified by preparative thin-layer chromatography (6×1000 μM plates) using a 20:1 mixture of CH$_2$Cl$_2$/MeOH as eluent to afford 0.26 g (93% yield) as an orange oil. LC-MS:=416.2 [M+H] 61% purity.

Preparative Example 130-C

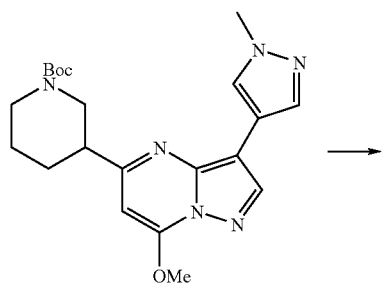

To a solution of 5-amino-3-methylisothiazole hydrochloride (0.15 g, 0.97 mmol) in dry DMSO (1.5 mL) at rt was added 60% NaH in oil (46 mg, 1.94 mmol) in one portion. The resulting mixture was stirred for 15 min at rt where upon the 7-methoxy adduct (0.20 g, 0.48 mmol) from Preparative Example 100-C was added in a single portion. The mixture was stirred for 12 h at rt, cooled to rt, and quenched with sat. aq. NH$_4$Cl (3 mL). The mixture was extracted with a mixture of 10% IPA/CH$_2$Cl$_2$ (3×20 ml) and the organic layers were combined. The organic layer was washed with brine (1×10 mL), dried (Na$_2$SO$_4$), filtered and concentrated under reduced pressure. The crude product was diluted with water (2 mL) and the resultant ppt was filtered and washed with water (2×1 mL). The ppt was dried under high vacuum to afford 0.22 g (93% yield) of a red/orange solid. LC-MS:= 495.3 [M+H] 99% purity.

Preparative Example 140-C

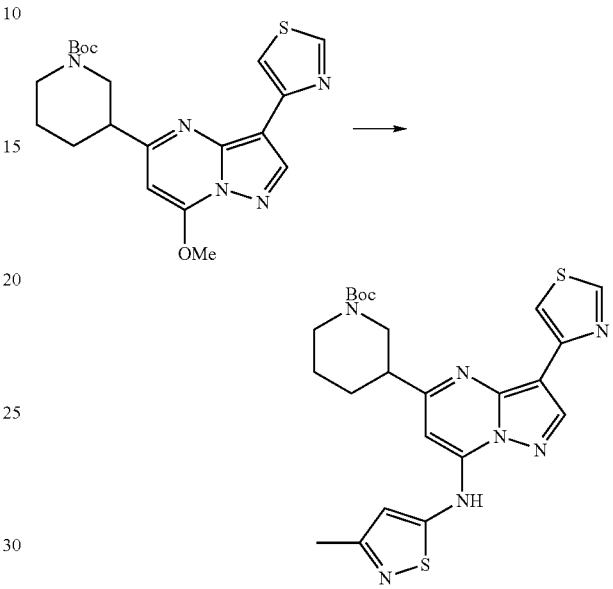

By essentially same procedure set forth in Preparative Example 130-C, the 7-methoxy adduct (0.28 g, 0.69 mmol) from Preparative Example 120-C was converted to 70 mg (20% yield) of an orange semisolid. MS=498.1 [M+H].

Example 10-C

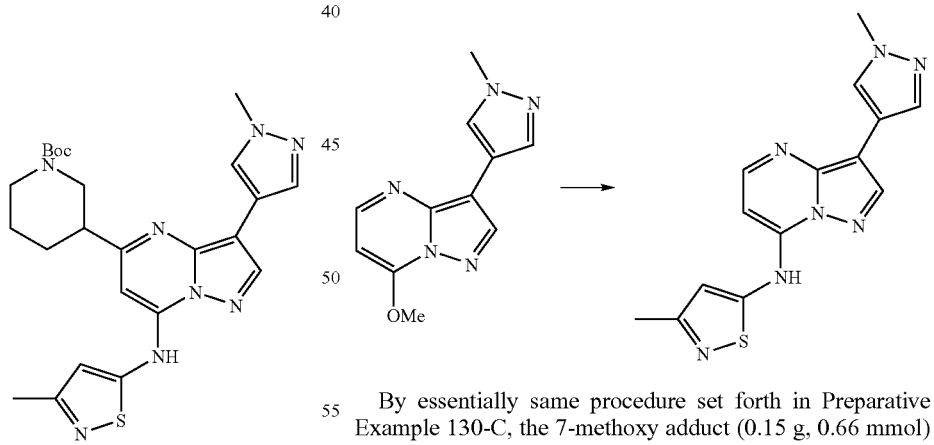

By essentially same procedure set forth in Preparative Example 130-C, the 7-methoxy adduct (0.15 g, 0.66 mmol) from Preparative Example 110-C was converted to 56 mg (27% yield) of a yellow solid. mp 152-155° C.; LC-MS=312.2. [M+H]; 85% purity.

Preparative Examples 150-C-230-C

Following the procedure set forth in Preparative Example 13 but utilizing the commercially available heteroaryl amines (as indicated) in Table 10-C with the 7-methoxy adduct from Preparative Example 100-C, the substituted pyrazolo[1,5-a]pyrimidine adducts were prepared (Products).

TABLE 10-C

| Prep. Ex. | Amine | Product | 1. Yield (%) 2. LC-MS |
|---|---|---|---|
| 150-C | 2-aminopyridine | | 1. 58 2. 475.3 |
| 160-C | 3-aminopyridine | | 1. 48 2. 475.3 |
| 170-C | 4-aminopyridine | | 1. 67 2. 475.3 |
| 180-C | 5-amino-3-methylisoxazole | | 1. 98 2. 479.3 |

TABLE 10-C-continued

| Prep. Ex. | Amine | Product | 1. Yield (%) 2. LC-MS |
|---|---|---|---|
| 190-C | 3-aminopyrazine | | 1. 33 2. 476.3 |
| 200-C | 2-amino-5-bromopyrimidine | | 1. 56 2. 556.3 |
| 210-C | 5-amino-1-ethylpyrazole | | 1. 98 2. 492.3 |
| 220-C | 2-amino-1,3,4-thiadiazole | | 1. 66 2. 482.3 |

TABLE 10-C-continued

| Prep. Ex. | Amine | Product | 1. Yield (%) 2. LC-MS |
|---|---|---|---|
| 230-C | 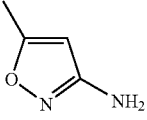 | 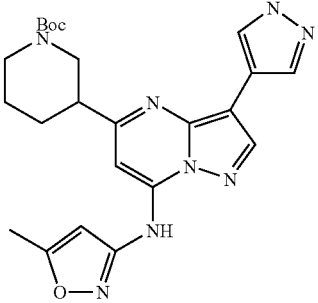 | 1. 90 2. 479.3 |

Preparative Example 231-C

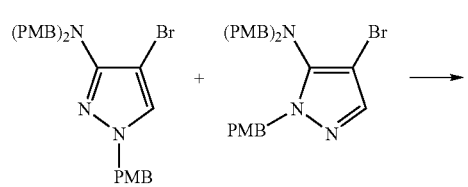

3-Amino-4-bromopyrazole (5 g, 30.9 mmol) and 4-methoxybenzyl chloride (21 g, 134 mmol, 4.3 equiv.) were combined in anhydrous DMF (25 mL) and added dropwise to a stirred suspension of sodium hydride (60% dispersion in mineral oil, 6.25 g, 156 mmol, 5 equiv.) in anhydrous DMF (50 mL). The resulting suspension was stirred 2 days at room temperature. Water (300 mL) was added slowly and the resulting mixture was extracted with ether (4×350 mL). The organic layers were combined, washed with brine, dried over anhydrous sodium sulfate and concentrated under reduced pressure. The crude product was dissolved in dichloromethane and purified by silica gel chromatography using a gradient from 10% to 20% ethyl acetate-hexanes. The product, a white solid, is obtained as a 60:40 mixture of the 1-benzylated-1H product and the 2-benzylated-2H product (14.96 g total, 93% yield).

Preparative Example 232-C

-continued

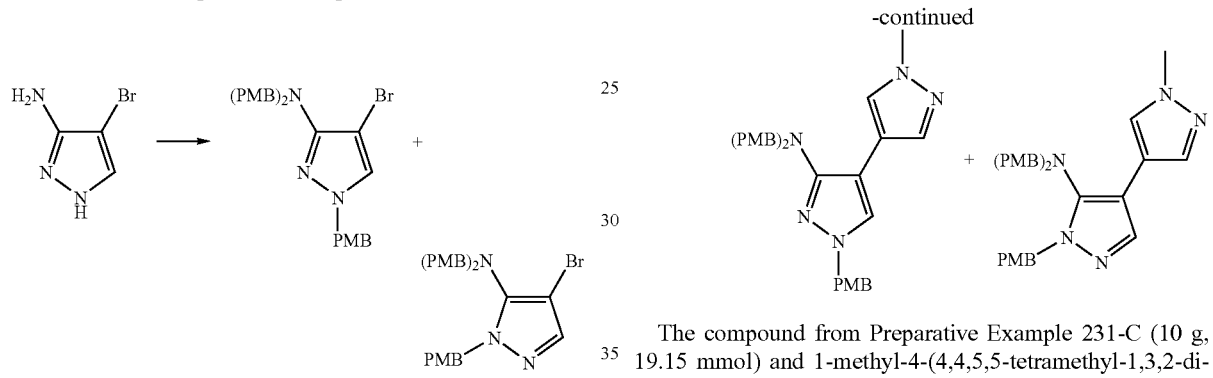

The compound from Preparative Example 231-C (10 g, 19.15 mmol) and 1-methyl-4-(4,4,5,5-tetramethyl-1,3,2-dioxaborolan-2-yl)-1H-pyrazole (11.95 g, 57.42 mmol, 3.0 equiv.) were combined in 120 mL dimethoxyethane. 2M sodium carbonate solution (30 mL, 60 mmol, 3.1 equiv.) was added followed by tetrakis(triphenylphosphine)palladium(0) (2.36 g, 2.04 mmol, 0.11 equiv.). The mixture was stirred 16 hours at 90° C. After cooling to room temperature, water (200 mL) and brine (50 mL) were added and the mixture was extracted with ethyl acetate (2×200 mL). The extracts were combined, washed with brine, dried over anhydrous sodium sulfate and concentrated under reduced pressure. The crude product was dissolved in dichloromethane and purified by silica gel chromatography using a gradient from 33% to 66% ethyl acetate-hexanes. The 1-benzylated-1H product ($R_f$=0.27 in 66% ethyl acetate-hexanes) elutes first, followed by the 2-benzylated-2H-product ($R_f$=0.19 in 66% ethyl acetate-hexanes). The product is obtained as a yellow solid (5.60 g total, 56% yield) with an isomeric ratio of 62:38.

Preparative Example 233-C

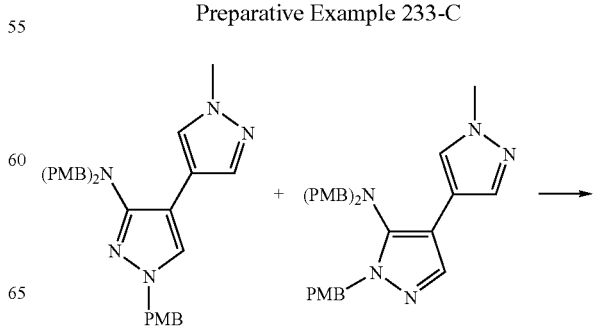

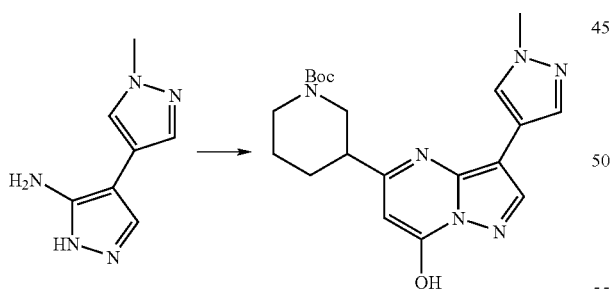

The compound from Preparative Example 232-C (4.3 g, 8.22 mmol) was dissolved in trifluoroacetic acid (70 mL) and stirred 17 hours at reflux. After cooling, the trifluoroacetic acid was removed under reduced pressure. The resulting residue was dissolved in tetrahydrofuran (100 mL), methanol (50 mL) and 4N aqueous sodium hydroxide solution (25 mL, 100 mmol, 12 equiv.). The mixture was stirred 4 hours at 70° C. then cooled to room temperature. The mixture was concentrated and the residue was suspended in brine (100 mL) and water (40 mL). This mixture was extracted with 20% isopropanol in ethyl acetate (8×100 mL). The extracts were combined, dried over anhydrous sodium sulfate, filtered and concentrated under reduced pressure. The crude product was dissolved in 10% methanol in dichloromethane and purified by silica gel chromatography using 10% methanol-dichloromethane followed by 10% 7N ammonia in methanol-dichloromethane. The product is obtained as a tan to brown solid (1.03 g, 77% yield).

Preparative Example 240-C

To a solution of aminopyrazole (0.74 g, 4.5 mmol) from Preparative Example 233-C in toluene (40 mL) in a pressure tube at rt was added β-keto ester (1.5 g, 5.0 mmol) from Preparative Example 1. The pressure tube was capped and heated to 110° C. and was stirred for 12 h. The mixture was cooled to rt and was concentrated under reduced pressure. The material was taken on crude to the next transformation. LC-MS:=399.2 [M+H]; 70% purity.

Preparative Example 250-C

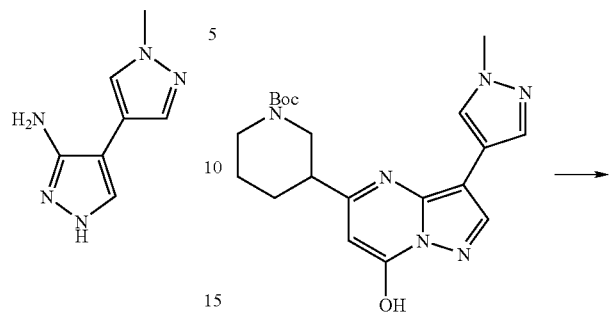

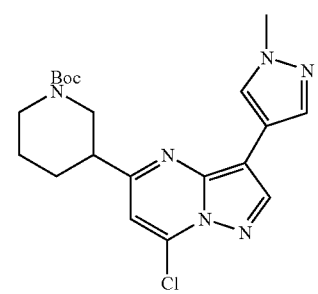

To a solution of 7-hydroxyl adduct (1.84 g, 4.5 mmol) from Preparative Example 240-C in POCl₃ (13 mL, 0.14 mol) at rt was added N,N-dimethylaniline (2 mL, 15.8 mmol). The resulting solution was stirred at rt for 12 h (until complete by TLC) and was concentrated under reduced pressure. The crude material was cooled to 0° C. and was treated with CH₂Cl₂ (50 mL) and sat. aq. NaHCO₃ (10 mL). The layers were separated and the aqueous layer was extracted with CH₂Cl₂ (2×50 mL). The organic layers were combined, dried (Na₂SO₄), filtered, and concentrated under reduced pressure. The crude product was purified by flash chromatography using a 1:1 mixture of hexanes/CH₂Cl₂ as eluent to afford 1.4 g (96% yield) of a brown semisolid. LC-MS:=317.2 [M+H]; 95% purity.

Preparative Example 251-C

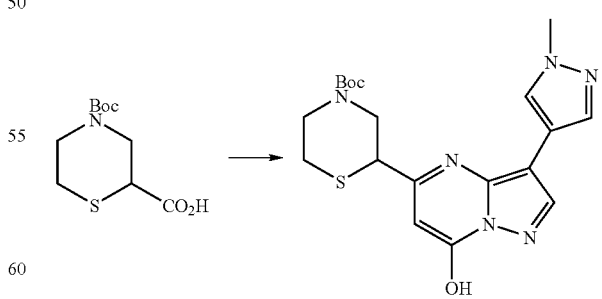

By essentially the same procedures set forth to make the compound from Preparative Example 250-C only starting with thiomorpholine carboxylic acid, the above compound was prepared.

Preparative Example 260-C

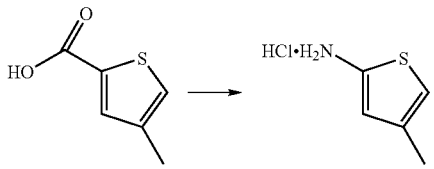

To a solution of 4-methylthiophene-2-carboxylic acid (5.0 g, 35.2 mmol) in t-BuOH (60 mL) was added DPPA (7.6 mL, 35.2 mmol) and Et$_3$N (4.9 mL, 35.2 mmol). The resulting mixture was heated to reflux and stirred for 48 h. The mixture was cooled to rt and was concentrated under reduced pressure. The crude material was purified by flash chromatography using a 3:1 mixture of hexanes/CH$_2$Cl$_2$ as eluent to afford 4.2 g (56% yield) as an orange oil.

The Boc derivative from above step (0.5 g, 2.3 mmol) was treated with 4M HCl/dioxane (25 mL) and was heated to 70° C. The mixture was stirred for 12 h, cooled to rt, and concentrated under reduced pressure to afford 0.32 g (93% yield) of the title compound. This material was used directly in subsequent coupling reactions.

Preparative Example 270-C

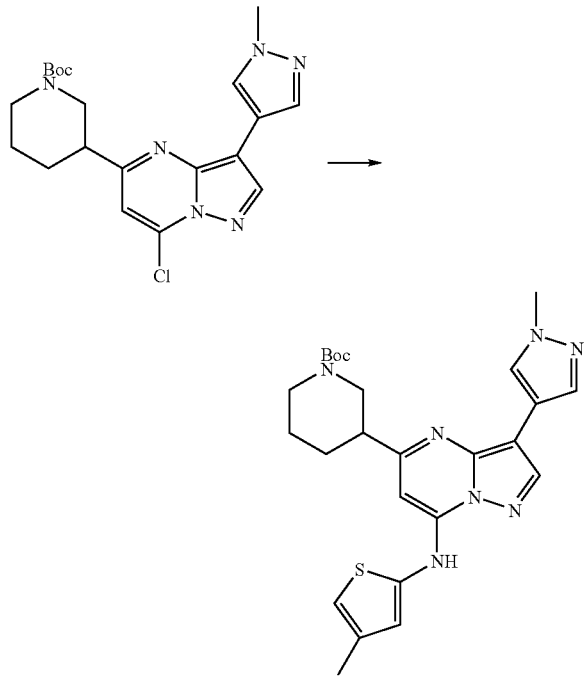

By essentially same procedure set forth in Preparative Example 130-C, the 7-chloro adduct (0.15 g, 0.35 mmol) from Preparative Example 250-C was treated with 2-amino-4-methyl thiophene hydrochloride (0.32 g, 2.1 mmol) from Preparative Example 260-C to afford 110 mg (64% yield) of a yellow semisolid. LC-MS=494.3 [M+H]; 80% purity.

Preparative Example 280-C

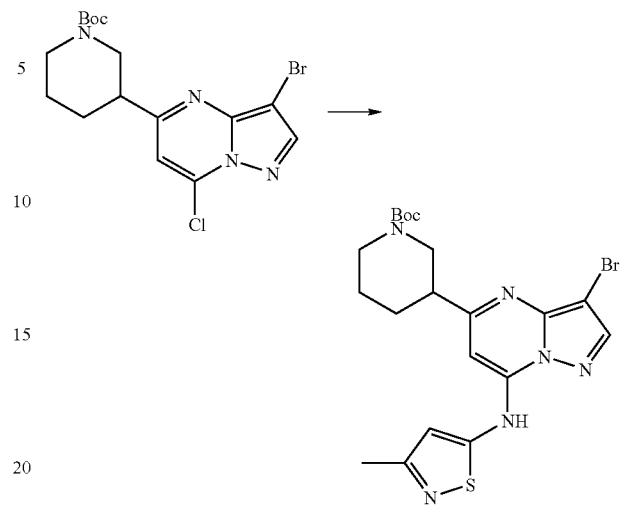

By essentially same procedure set forth in Preparative Example 130-C, the 7-chloro adduct (0.40 g, 0.96 mmol) from Preparative Example 60-C was treated with 5-amino-3-methylisothiazole hydrochloride (0.28 g, 1.9 mmol) to afford 430 mg (91% yield) of a yellow semisolid. LC-MS=495.3 [M+H]; 80% purity.

Example 20-C

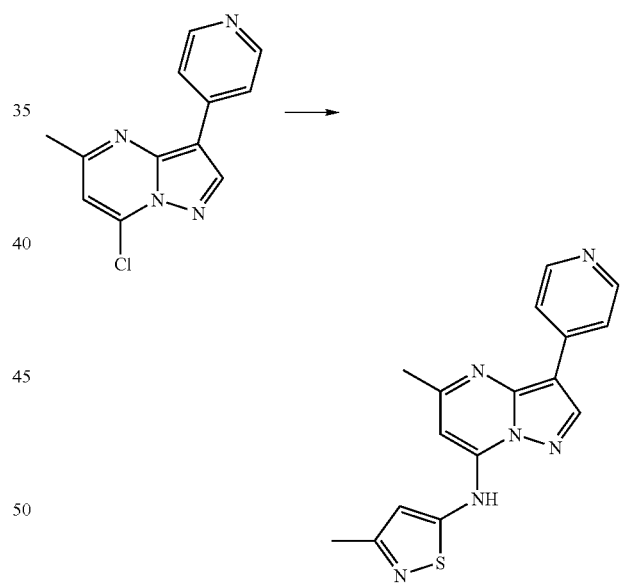

By essentially same procedure set forth in Preparative Example 130-C, the 7-chloro adduct (0.12 g, 0.49 mmol) from was treated with 5-amino-3-methylisothiazole hydrochloride (0.15 g, 0.98 mmol) to afford 38 mg (24% yield) of an orange solid. mp 165-167° C.; LC-MS=323.2 [M+H]; 98% purity.

Preparative Example 290-C

Following the procedure set forth in Preparative Example 130-C but utilizing the commercially available heteroaryl amines (as indicated) in Table 20-C with the 7-chloro adduct from Preparative Example 250-C, the substituted pyrazolo[1,5-a]pyrimidine adducts were prepared (Products).

TABLE 20-C

| Prep. Ex. | Amine | Product | 1. Yield (%) 2. LC-MS |
|---|---|---|---|
| 290-C | 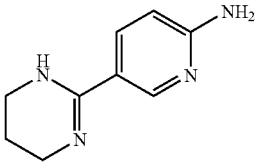 | 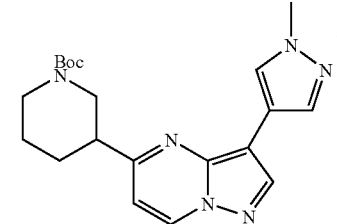 | 1. 53 2. 557.3 |
| 291-C | 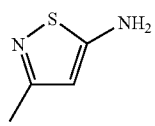 | 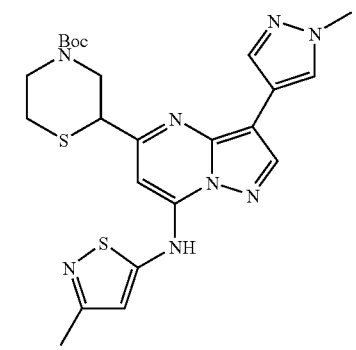 | |

Preparative Example 300-C

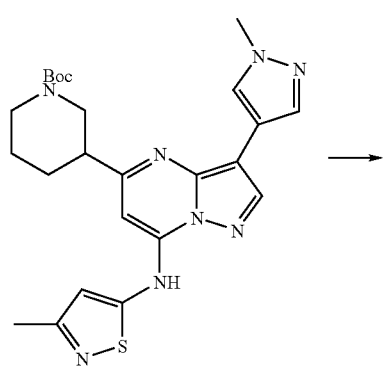

→

To a solution of Boc adduct (54 mg, 0.11 mmol) from Preparative Example 130-C in CH$_2$Cl$_2$ (5 mL) at rt was added t-BuNH$_2$ (0.41 mL, 3.9 mmol). The mixture was stirred for 15 min whereupon Br$_2$ (5 μL, 0.099 mmol) was added dropwise and the reaction was stirred for 1.5 h (until complete by TLC). The mixture was concentrated to dryness and the crude product was purified by preparative thin-layer chromatography using 4×1000 μM plates with a 24:1 mixture of CH$_2$Cl$_2$/MeOH as eluent to afford 25 mg (35% yield) of the title compound. LC-MS=653.4 [M+H]; 99% purity.

Example 30-C

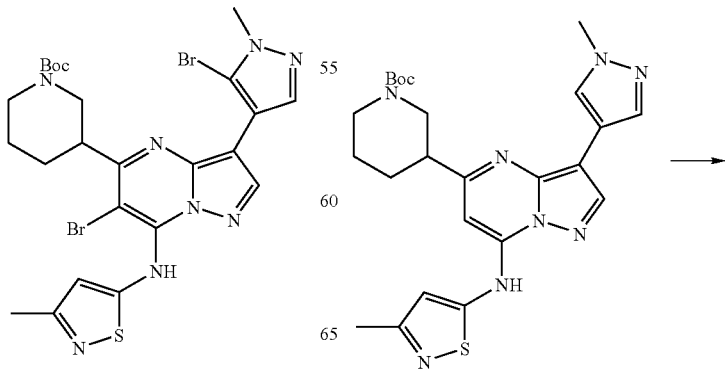

-continued

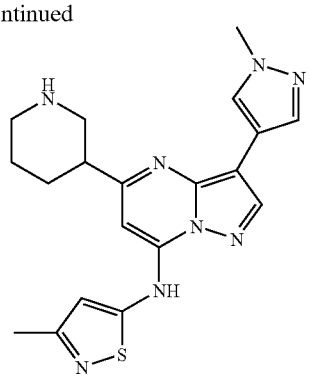

To a mixture of pyrazole adduct (120 mg, 0.24 mmol) from Preparative Example 130-C in CH$_2$Cl$_2$(2 mL) at 0° C. was added TFA (0.6 mL) dropwise. The resulting mixture was stirred for 3 h at rt and concentrated under reduced pressure. The crude material was dissolved in 7M NH$_3$ in MeOH (3 mL) and was stirred for 2 h. The mixture was concentrated under reduced pressure and placed under high vacuum. The crude product was purified by preparative thin-layer chromatography (4×1000 μM plates) using a 10:1 mixture of CH$_2$Cl$_2$/MeOH (7M NH$_3$) as eluent to afford 20 mg (21% yield) as maize solid. mp 167-170° C.: LC-MS:=395.2 [M+H] 95% purity.

Examples 40-C-170-C

Following the procedure set forth in Example 30-C utilizing the appropriate Boc derivatives shown in Column 2, the substituted pyrazolo[1,5-a]pyrimidine adducts were prepared (Products) in Table 30-C.

TABLE 30-C

| Ex. | Column 2 | Product | 1. Yield (%) 2. LC-MS 3. mp (° C.) |
|---|---|---|---|
| 40-C | | | 1. 38 2. 375.2 3. 124-126 |
| 50-C | | | 1. 26 2. 375.2 3. 169-171 |
| 60-C | | | 1. 36 2. 375.2 3. 200-202 |

TABLE 30-C-continued
| Ex. | Column 2 | Product | 1. Yield (%) 2. LC-MS 3. mp (° C.) |
|---|---|---|---|
| 70-C | 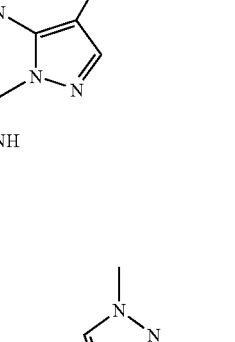 | 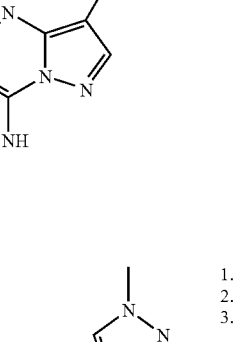 | 1. 78 2. 379.2 3. 180-182 |
| 80-C | 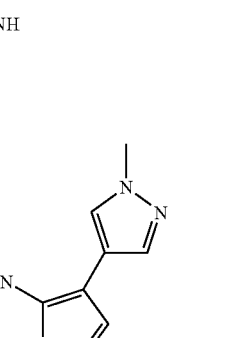 | 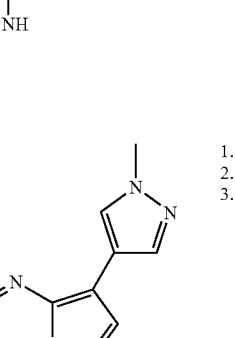 | 1. 92 2. 376.2 3. 119-121 |
| 90-C | 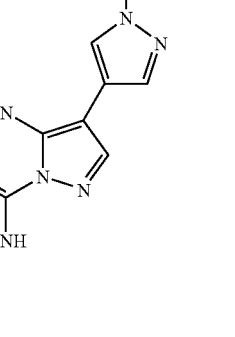 | 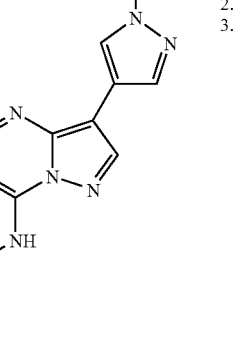 | 1. 71 2. 454.1 3. 157-159 |
| 100-C | 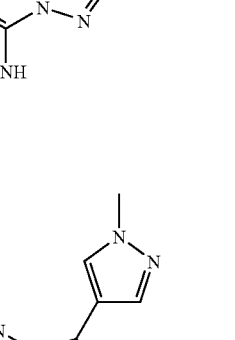 | 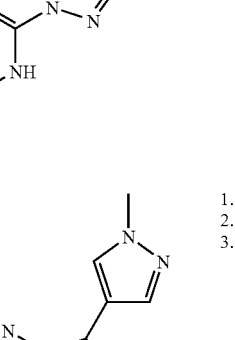 | 1. 98 2. 392.2 3. 171-174 |

TABLE 30-C-continued

| Ex. | Column 2 | Product | 1. Yield (%) 2. LC-MS 3. mp (° C.) |
|---|---|---|---|
| 110-C | | | 1. 33 2. 382.2 3. 130-132 |
| 120-C | | | 1. 70 2. 379.2 3. 118-121 |
| 130-C | | | 1. 46 2. 457.3 3. 172-175 |
| 140-C | | | 1. 34 2. 394.2 3. 121-123 |

TABLE 30-C-continued

| Ex. | Column 2 | Product | 1. Yield (%) <br> 2. LC-MS <br> 3. mp (° C.) |
|---|---|---|---|
| 150-C | | | 1. 27 <br> 2. 398.2 <br> 3. 156-158 |
| 160-C | | | 1. 42 <br> 2. 395.2 <br> 3. 168-171 |
| 170-C | | | 1. 32 <br> 2. 563.3 |
| 171-C | | | $^1$H NMR (DMSO) δ 8.46 (s, 1H), 8.11 (s, 1H), 7.96 (s, 1H), 7.13 (s, 1H), 6.72 (s, 1H), 4.13-4.10 (m, 1H), 3.89 (s, 3H), 3.50-3.46 (m, 1H), 3.30-3.15 (m, 2H), 2.95-2.88 (m, 1H), 2.83-2.77 (m, 1H), 2.69-2.65 (m, 1H), 2.38 (s, 3H); MH$^+$ = 413. |

Examples 180-C and 190-C

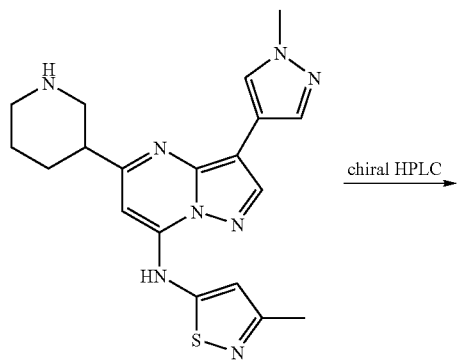

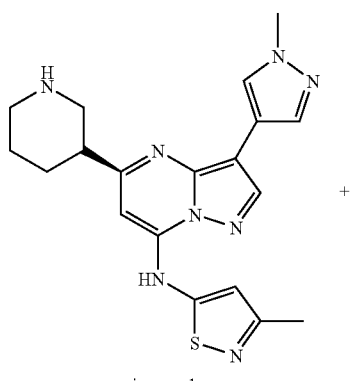
isomer 1

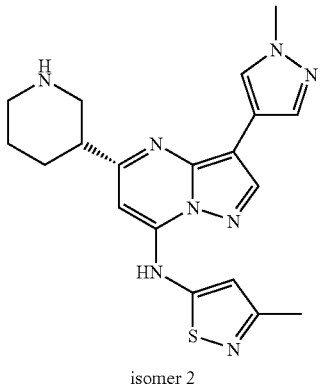
isomer 2

20 mg of Example 30-C was injected on a semipreparative Chiralcel AD column. Chromatography with mobile phase 70:30 hexane/2-propanol with 0.2% diethylamine afforded two isomers: fast eluting (isomer 1) Example 180-C: 7 mg, yellow solid; LC-MS: 395.2 [M+H]; purity 99% and a slower eluting (isomer 2) Example 190-C: 8 mg, yellow solid; LC-MS: 395.2 [M+H]; purity 99%.

Examples 200-C and 210-C

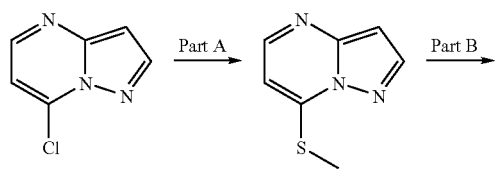

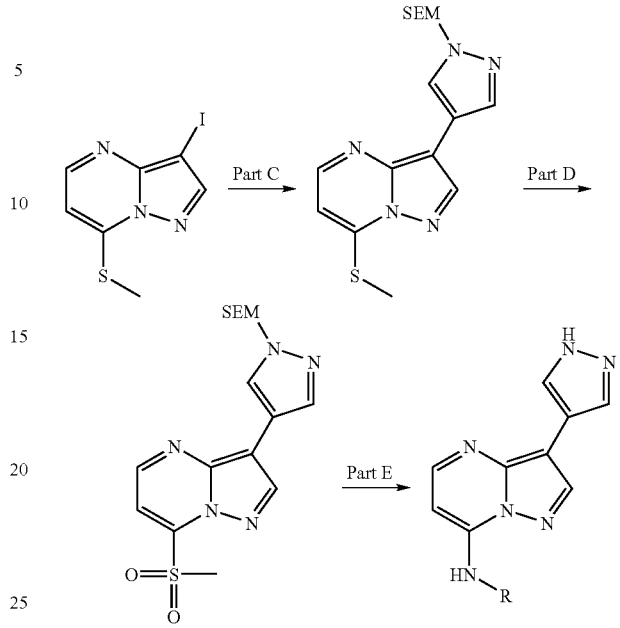

Part A

To a solution of 7-chloro-pyrazolo[1,5-a]pyrimidine (0.66 g) in DMSO (10 mL) was added sodium methanethiolate (0.45 g) in one portion. The resulting suspension was heated at 90° C. for 16 hr, allowed to cool and then was extracted with ethyl acetate (3×50 mL). The organic phase was washed with water, brine and then dried (sodium sulfate). Chromatographic purification (silica gel, 25% ethyl acetate in hexanes) afforded the title compound as a yellow orange solid (0.42 g). $^1$H-NMR (400 MHz, DMSO-$d_6$) δ 8.81 (dd, 1H), 8.08 (dd, 1H), 6.90 (d, 1H), 6.50 (dd, 1H), 2.55 (s, 3H). LCMS: MH$^+$=166.

Part B

To a solution of 7-methylsulfanyl-pyrazolo[1,5-a]pyrimidine (0.42 g, 2.54 mmol, 1.00 equiv) in acetonitrile (12 mL) at room temperature was added N-iodosuccinimide (0.6 g, 2.7 mmol, 1.05 equiv) in one portion. After 30 min at rt, the reaction was concentrated affording the title compound as a yellow orange solid. The product was used in the next step without purification. $^1$H-NMR (400 MHz, DMSO-$d_6$) δ 8.83 (d, 1H, J=8.0 Hz), 8.17 (s, 1H), 6.98 (d, 1H, J=8.0 Hz), 2.55 (s, 3H). LCMS: MH$^+$=292.

Part C

A mixture of 3-iodo-7-methylsulfanyl-pyrazolo[1,5-a]pyrimidine (0.21 g, 0.73 mmol, 1.00 equiv), boronate (0.31 g, 0.95 mmol, 1.3 equiv), PdCl$_2$(dppf) (0.059 g, 0.07 mmol, 10 mol %) and potassium phosphate monohydrate (0.34 g, 1.5 mmol, 2.0 equiv) in 1,2-DME (6 mL) and water (1 mL) was stirred under Argon at 100° C. for 12 hr. The mixture was allowed to cool to room temperature and then was partitioned between ethyl acetate and water, washed with brine and dried (sodium sulfate). Chromatographic purification (silica gel, 20% ethyl acetate in hexanes) afforded 0.2 g of the title compound. LCMS: MH$^+$=362.

Part D

To a solution of 7-methylsulfanyl-3-[1-(2-trimethylsilanyl-ethoxymethyl)-1H-pyrazol-4-yl]-pyrazolo[1,5-a]pyrimidine (0.2 g, 0.55 mmol, 1.00 equiv) in DCM (10 mL) at rt was added m-CPBA (0.25 g, 1.1 mmol, 2.0 equiv) in one portion. The resulting mixture was allowed to stir for 30 min at rt and then was concentrated. The residue was partitioned between ethyl acetate and water and the organic phase was washed with aq. sodium bicarbonate (2×), brine and dried (sodium sulfate). Concentration afforded the title compound as an orange solid that was used directly in the next step.

Part E

To a solution of isothiazole (1.15 equiv) in DMSO (2 mL) was added NaH (2.65 equiv). The resulting suspension was stirred 5 min, then sulfone (1 equiv) from Part D was added. The reaction was quenched with saturated aq. NH$_4$Cl and extracted with ethyl acetate. The crude residue was treated with 2N HCl dioxane at 50° C. for 10 min, concentrated, purified by Prep-LC and then converted to a hydrochloric salt.

By the procedures outlined in Part A-E, the compounds shown Column 2 of Table 40-C were prepared.

TABLE 40-C

| Example | Column 2 | Exact mass | MS m/z (M + H) | HPLC MS $t_R$ |
|---|---|---|---|---|
| 200-C | | 297.1 | 298.1 | 0.96 |
| 210-C | | 366.1 | 367.1 | 0.79 |

Preparative Example 310-C

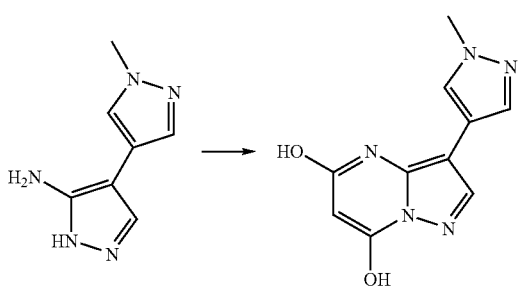

To a suspension of pyrazole from Preparative Example 233-C (4.0 g, 24.5 mmol, 1.00 equiv), dimethylmalonate (3.1 mL, 27.0 mmol, 1.1 equiv) in EtOH (74 mL) at rt was added 25% NaOMe in MeOH (11.2 mL). The mixture was heated at reflux overnight (16 hr), allowed to cool to room temperature and then concentrated. The residue was dissolved in a minimum amount of water (~100 mL) and then was treated with 1N HCl until the pH was ~2-3. The resulting ppt was collected by filtration and dried affording the title compound as a tan solid (4.9 g, 87%). LCMS: MH$^+$=232.

Example 320-C

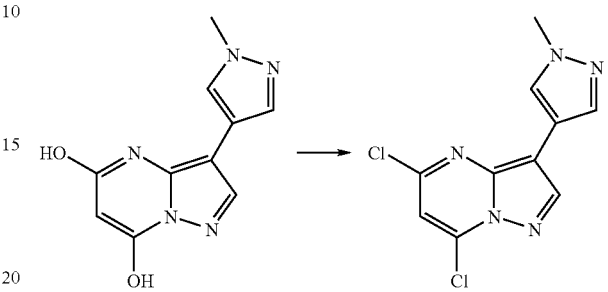

A suspension of 5,7-dihydroxypyrazolopyrimidine from Preparative Example 310-C (4.2 g, 18.2 mmol, 1.00 equiv), N,N-diethylaniline (9 mL) and PCl$_5$ (1.94 g, 9.32 mmol, 0.5 equiv) in POCl$_3$ (170 mL was heated at 120° C. in a sealed vessel for 20 h. After the solution was allowed to cool, volatiles were removed under reduced pressure. The residue was dissolved in DCM and then carefully added to aq. sodium bicarbonate. The organic phase was rinsed with water, brine and dried. Concentration and purification by flash chromatography (silica gel) afforded the title compound as a bright yellow solid (3.7 g, 76%). LCMS: MH+=268.

Preparative Example 330-C

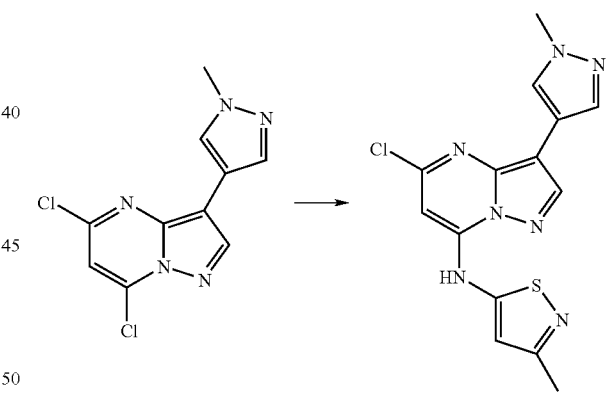

To a solution of aminoisothiazole (0.66 g, 2.0 equiv) in DMSO (30 mL) at rt was added NaH (0.29 g of 60% dispersion in oil, 2.5 equiv) in one portion. After ca. 10 min, the compound from Preparative Example 320-C (0.78 g, 1.00 equiv) was added in one portion. After 30 min at room temperature, the reaction was quenched with sat. aq. ammonium chloride and then extracted with 10% IPA/DCM (twice). The combined organic layers were washed with water, brine and dried (sodium sulfate). After concentration the residue was purified by column chromatography (silica gel, 80% EtOAc/hexane→EtOAc) to give the title compound 2 as a yellow solid 0.85 g (86%). $^1$H-NMR (400 MHz, DMSO-d$_6$) δ 11.63 (bs, 1H), 8.59 (s, 1H), 8.11 (s, 1H), 7.91 (d, 1H), 7.32 (s, 1H), 6.63 (s, 1H), 3.91 (s, 3H) and 2.41 (s, 3H). HPLC-MS $t_R$=1.64 Min (UV$_{254 nm}$). Mass calculated for formula C14H12ClN7S 345.06, observed LC/MS m/z 346.0 (M+H).

Preparative Example 340-C

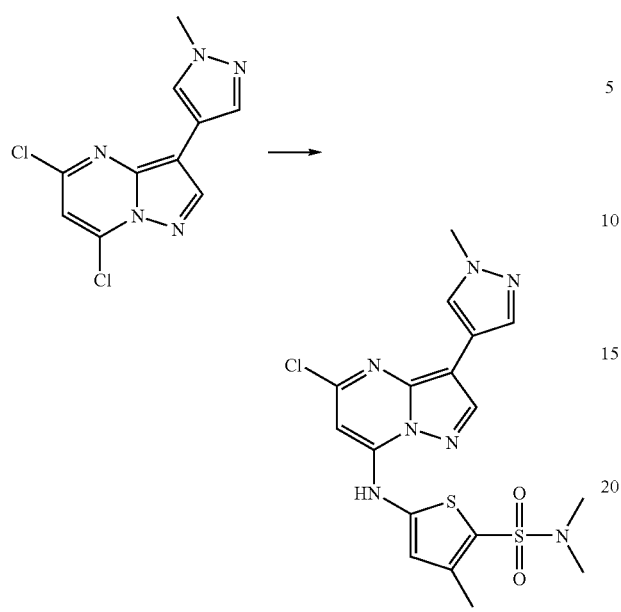

By essentially the same procedure set forth in Preparative Example 330-C, the compound shown above was prepared.

Example 220-C

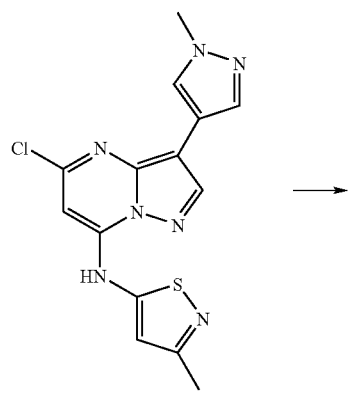

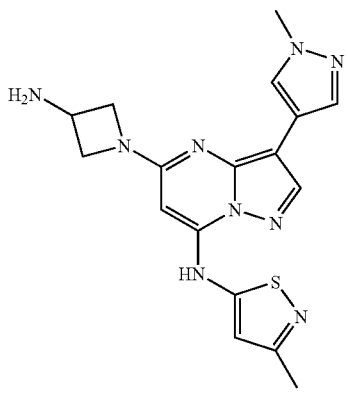

To a solution of the compound from Preparative Example 330-C (0.03 g, 0.087 mmol) in DMSO (1 mL) in a sealed tube vessel was added 3-aminoazetidine (3 equiv) and triethylamine (5 equiv). The tube was sealed and heated via a microwave at 125° C. for 60 min. LC-MS analysis indicated the reaction was complete. Purification by Prep-LC and conversion to a hydrochloric salt afforded compound 2. HPLC-MS $t_R$=2.58 Min (UV $_{254\ nm}$). Mass calculated for formula $C_{17}H_{19}N_9S$ 381.15, observed LC/MS m/z 382.1 (M+H).

Examples 230-C-430-C

By essentially the same procedure outline in Example 220-C only substituting the appropriate amine, the compounds shown in Column 2 of Table 50-C were prepared.

TABLE 50-C

| Example | Column 2 | Exact mass | MS m/z (M+H) | HPLC MS $t_R$ |
|---|---|---|---|---|
| 230-C | | 381.15 | 382.1 | 2.58 |

TABLE 50-C-continued

| Example | Column 2 | Exact mass | MS m/z (M + H) | HPLC MS $t_R$ |
|---|---|---|---|---|
| 240-C | | 395.16 | 396.1 | 1.94 |
| 250-C | | 409.18 | 410.1 | 2.08 |
| 260-C | | 409.18 | 410.1 | 2.12 |
| 270-C | | 395.16 | 396.1 | 1.98 |

TABLE 50-C-continued

| Example | Column 2 | Exact mass | MS m/z (M + H) | HPLC MS $t_R$ |
|---|---|---|---|---|
| 280-C | | 424.18 | 425.2 | 3.72 |
| 290-C | | 410.16 | 411.1 | 3.21 |
| 300-C | | 409.18 | 410.2 | 2.75 |
| 310-C | | 407.16 | 408.1 | 2.67 |

TABLE 50-C-continued

| Example | Column 2 | Exact mass | MS m/z (M + H) | HPLC MS $t_R$ |
|---|---|---|---|---|
| 320-C | | 395.16 | 396.1 | 2.62 |
| 330-C | | 423.2 | 424.1 | 3.31 |
| 340-C | | 423.2 | 424.1 | 2.85 |
| 350-C | | 423.2 | 424.1 | 2.92 |

TABLE 50-C-continued

| Example | Column 2 | Exact mass | MS m/z (M + H) | HPLC MS $t_R$ |
|---|---|---|---|---|
| 360-C | | 395.16 | 396.1 | 2.62 |
| 370-C | | 439.19 | 440.2 | 2.76 |
| 380-C | | 515.19 | 516.1 | 3.38 |

TABLE 50-C-continued

| Example | Column 2 | Exact mass | MS m/z (M + H) | HPLC MS $t_R$ |
|---|---|---|---|---|
| 390-C | | 487.16 | 488.2 | 3.06 |
| 400-C | | 501.17 | 502.1 | 3.48 |
| 410-C | | 515.19 | 516.1 | 3.68 |

TABLE 50-C-continued
| Example | Column 2 | Exact mass | MS m/z (M + H) | HPLC MS $t_R$ |
|---|---|---|---|---|
| 420-C | 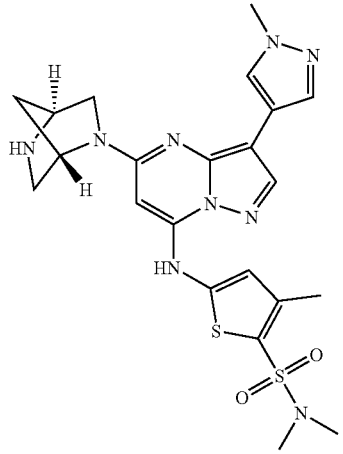 | 513.17 | 514.2 | 3.27 |
| 430-C | 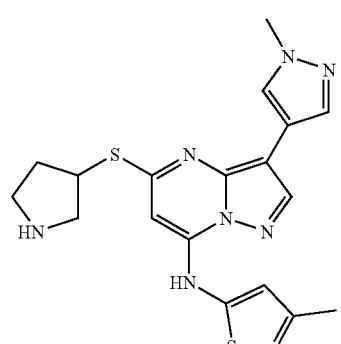 | 412.13 | 413.0 | 3.12 |
Example 440-C
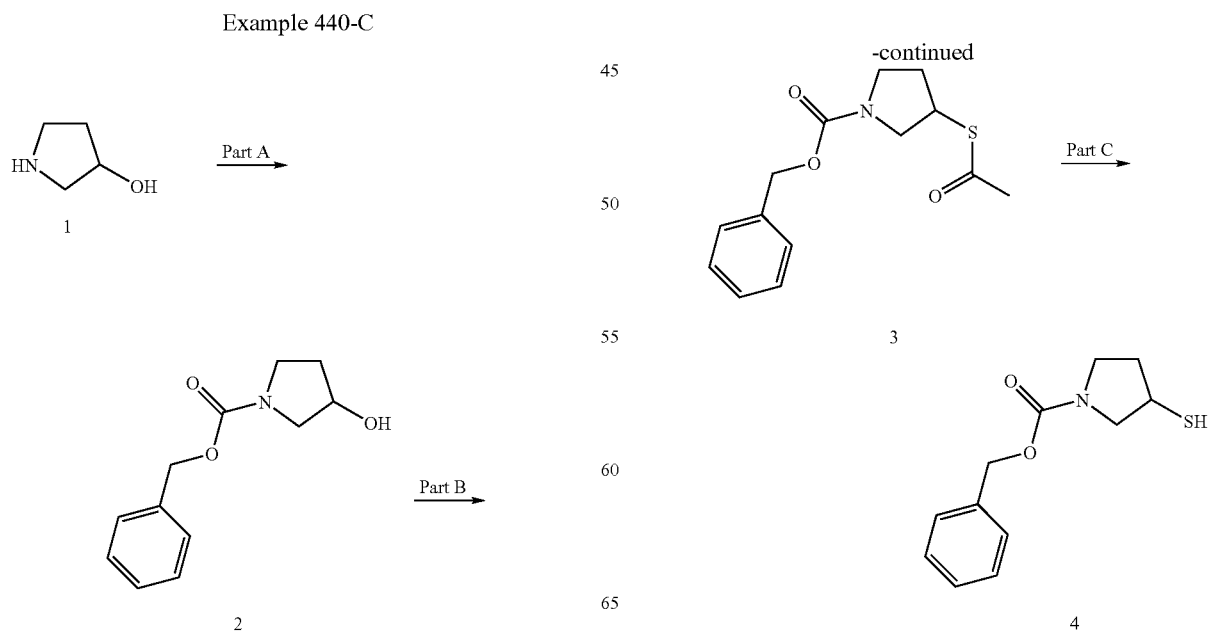

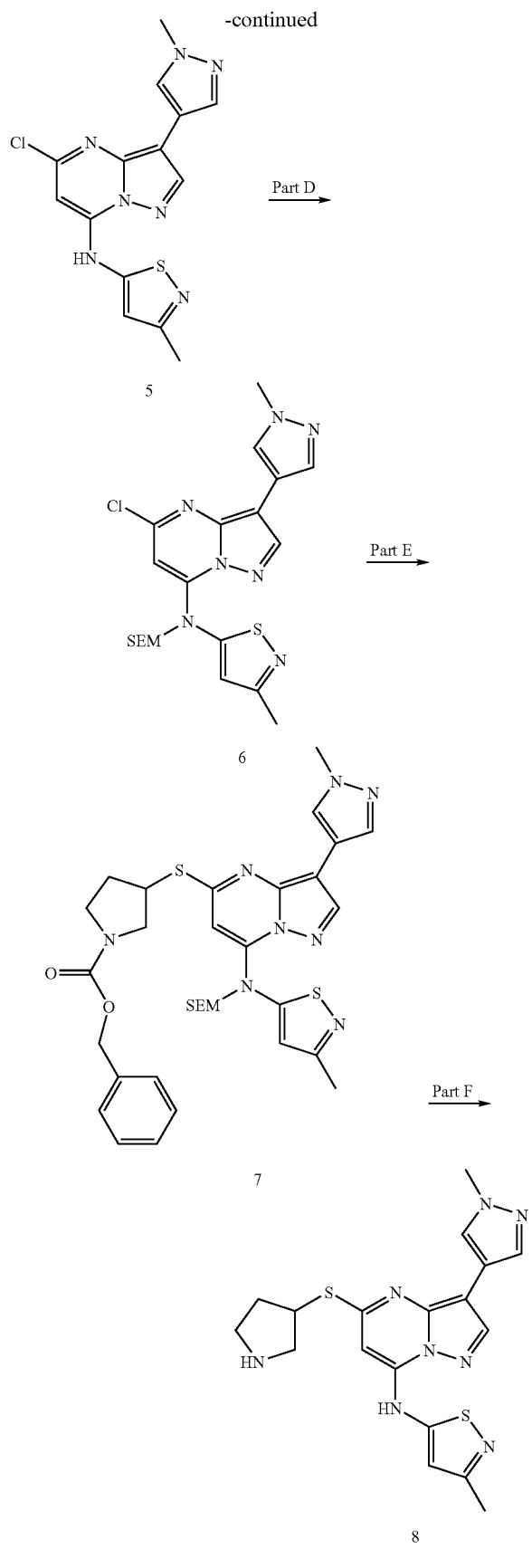

Part A:

To compound 1 (2.1 g, 24.1 mmol) in DCM (150 mL) was added triethylamine (1.2 equiv). The resulting solution was cooled to 0° C.(ice-bath) and stirred at 0° C. for 10 min, then added benzyl chloroformate (1.2 equiv). The reaction mixture was stirred at 0° C. for 60 min at which time LC-MS analysis indicate that the reaction was complete. After concentration the residue was purified by column chromatography ($SiO_2$, 60% ethyl acetate/hexanes) afforded compound 2 as a clear oil 4.0 g (75%).

Part B:

A solution of compound 2 (1 g, 4.52 mmol) and triphenyphosphine (1.1 equiv) in anh. THF (30 mL) was treated at 0 C. with diisopropyl azodicarboxylate (1.1 equiv) for 10 min, thioacetic acid (1.1 equiv) was added and the reaction mixture allowed to slowly warm to rt. The reaction mixture was stirred at room temperature overnight. After concentration the residue was purified by column chromatography ($SiO_2$, 40% ethyl acetate/hexanes) afforded compound 3 as a clear oil 1.2 g (95%).

Part C:

A solution of compound 3 (1.2 g, 4.26 mmol) in methanol (30 mL) was treated with potassium carbonate (1.2 equiv). The resulting solution was stirred at room temperature for 16 hr, at which time LC-MS analysis indicated that the reaction was complete. After concentration the residue was purified by column chromatography ($SiO_2$, 40% ethyl acetate/hexanes) afforded compound 4 as a clear oil 0.26 g (26%).

Part D:

Compound 5 was synthesized via the synthetic method described in Preparative example 3 (Part A).

To compound 5 (0.29 g, 0.84 mmol) in dichloroethane (10 mL) was added DIEA (1.2 equiv) at room temperature. The resulting solution was stirred at room temperature for 10 min, and then added 2-(trimethylsilyl)-ethoxymethyl chloride (1.2 equiv). The resulting mixture was stirred at room temperature for 4 hr at which time LC-MS analysis indicated the reaction was complete. After concentration the residue was purified by column chromatography ($SiO_2$, 80% ethyl acetate/hexanes) afforded compound 6 as an orange oil 0.17 g (43%).

Part E:

A mixture of compound 7 (35 mgs, 0.074 mmol, 1 equivalent), compound 4 (1.4 equivalent), $PdCl_2(dppf)$ (0.07 equiv), sodium tert-butoxide (1.1 equiv) in 1,2-dimethoxyethane (1 ml) was stirred at 85° C. under Argon for 16 hr. The reaction mixture was cooled to room temperature, filtered through celite and the filtrate concentrated. The residue was taken back up in ethyl acetate and washed with water, brine, dried over anhydrous sodium sulfate and concentrated to afford crude compound 7, which was used in the next step directly without further purification.

Part F:

To a solution of compound 7 in THF (2 mL) was added 4N HCl in dioxane (2 mL) at rt. The resulting solution was heated at 60° C. for 60 min at which time LC-MS analysis indicated the reaction was complete. The mixture was cooled to 25° C. and concentrated. Purification by Prep-LC and conversion to a hydrochloric salt afforded compound 8, Example 440-C.

HPLC-MS $t_R$=3.10 Min (UV $_{254\ nm}$). Mass calculated for formula $C_{18}H_{20}N_8S_2$ 412.13, observed LC/MS m/z 413.0 (M+H).

Preparative Example 631-C

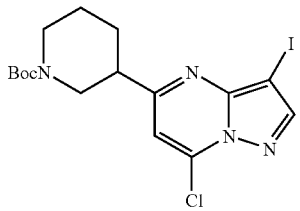

By essentially same procedure set forth in Preparative Example 60-C, using N-iodosuccinimide instead of N-bromosuccinimide, the title compound was prepared.

Preparative Example 641-C

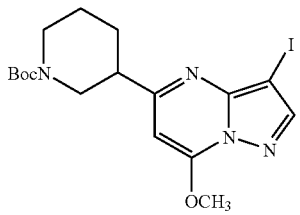

By essentially same procedure set forth in Preparative Example 80-C, starting from the compound from Preparative Example 631-C, the title compound was prepared.

Preparative Example 645-C

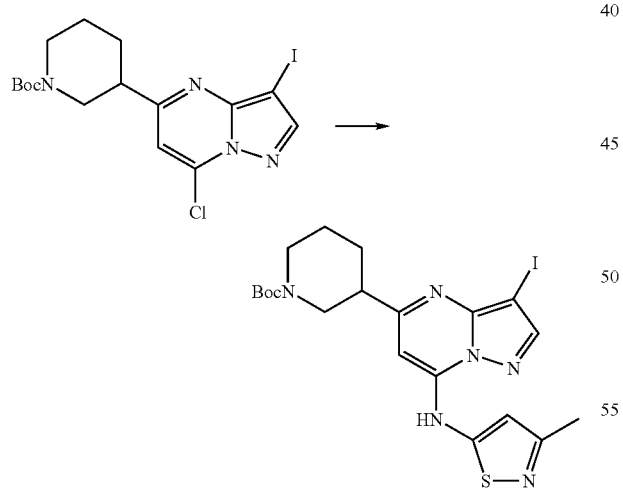

A mixture of the product from Preparative Example 631-C (2.40 g, 5.20 mmol), 5-amino-3-methylisothiazole hydrochloride (1.01 g, 6.70 mmol) and $K_2CO_3$ (2.15 g, 15.60 mmol) in anhydrous $CH_3CN$ (30 mL) was stirred and refluxed under $N_2$ for 72 hr. $CH_2Cl_2$ (200 mL) was then added, the mixture was filtered through Celite, the solvent was evaporated, and the residue was purified by column chromatography on silica gel with 10:1 $CH_2Cl_2$/EtOAc as eluent. Canary yellow solid (580 mg, 21%) was obtained. LC-MS: 541 [M+H].

Preparative Example 646-C

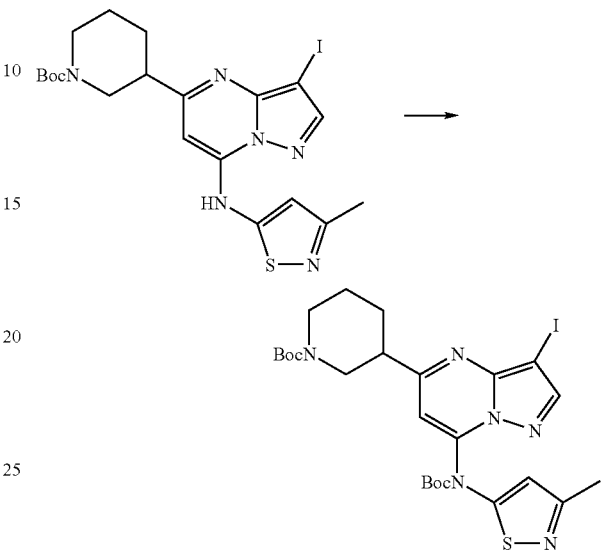

$Boc_2O$ (305 mg, 1.40 mmol) was added to a stirred solution of the product from Preparative Example 645-C (580 mg, 1.07 mmol) and 4-dimethylamino pyridine (146 mg, 1.20 mmol) in anhydrous $CH_2Cl_2$ (10 mL). The mixture was stirred at 25° C. for 2 hr, then it was poured into saturated aqueous $NaHCO_3$ solution (60 mL), extracted with $CH_2Cl_2$ (3×10 mL), dried over $Na_2SO_4$, and filtered. The solvents were evaporated and the residue was purified by column chromatography on silica gel with 25:1 $CH_2Cl_2$/EtOAc as eluent. Canary yellow solid (420 mg, 61%) was obtained.

Preparative Example 647-C

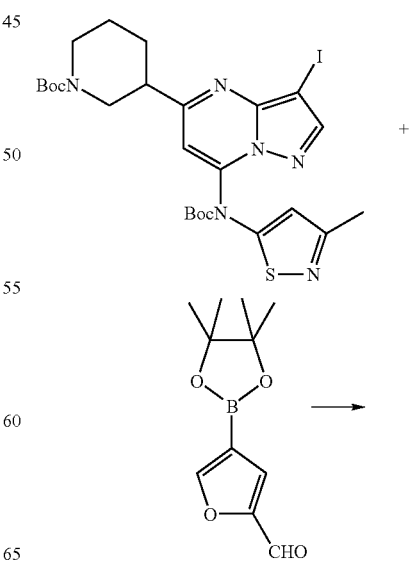

-continued

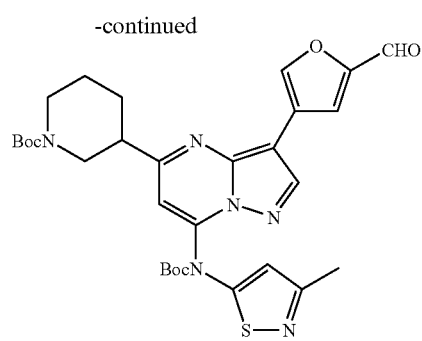

A mixture of the product from Preparative Example 646-C (400 mg, 0.63 mmol), the boronate (208 mg, 0.94 mmol), PdCl₂dppf.CH₂Cl₂ (49 mg, 0.06 mmol), and K₃PO₄ (530 mg, 2.50 mmol) in 1,2-dimethoxyethane (10 mL) and H₂O (2 mL) was stirred and refluxed under N₂ for 2 hr. The solvents were evaporated and the residue was purified by column chromatography on silica gel with 2:1 hexane/EtOAc as eluent. Pale yellow solid (42 mg, 11%) was obtained. LC-MS: 609 [M+H].

Preparative Example 648-C

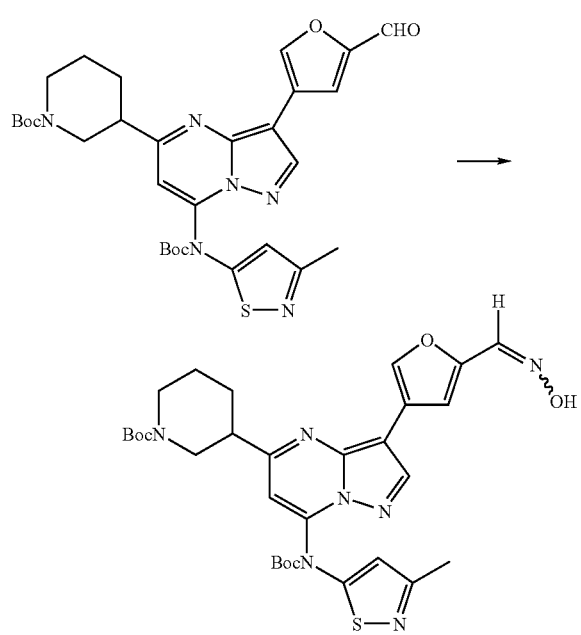

A mixture of the product from Preparative Example 647-C (42 mg, 0.069 mmol), NH₂OH.HCl (7 mg, 0.10 mmol), and triethylamine (0.2 mL) in CH₂Cl₂ (1 mL) and MeOH (1 mL) was stirred in a closed flask at 25° C. for 4 hr. The solvent was evaporated and the residue was chromatographed on silica gel with 2:1 hexane/EtOAc as eluent. Yellow solid (30 mg, 70%) was obtained.

Preparative Example 650-C

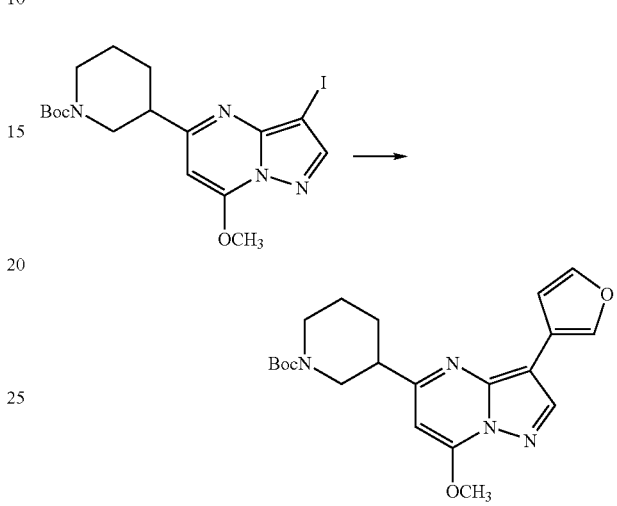

A mixture of the product from Preparative Example 641-C (300 mg, 0.66 mmol), 3-furylboronic acid (110 mg, 0.98 mmol), PdCl₂dppf.CH₂Cl₂ (54 mg, 0.06 mmol), and K₃PO₄ (560 mg, 2.64 mmol) in 1,2-dimethoxyethane (10 mL) and H₂O (2 mL) was stirred and refluxed under N₂ for 5 hr. The solvents were evaporated and the residue was purified by column chromatography on silica gel with 25:1 CH₂Cl₂/MeOH as eluent. Pale yellow solid (175 mg, 67%) was obtained. LC-MS: 399 [M+H].

Preparative Examples 651-C-652-C

By essentially same procedure set forth in Preparative Example 650-C, only using different boron reagents given in Column 1 for the Suzuki couplings with the intermediate from preparative Example 641-C, compounds given in Column 2 of Table 100-C were prepared.

TABLE 100-C

| Prep. Ex. | Column 1 | Column 2 | Data |
|---|---|---|---|
| 651-C | ![boronate] | ![product] | LCMS: MH⁺ = 435 |

TABLE 100-C-continued

| Prep. Ex. | Column 1 | Column 2 | Data |
|---|---|---|---|
| 652-C | 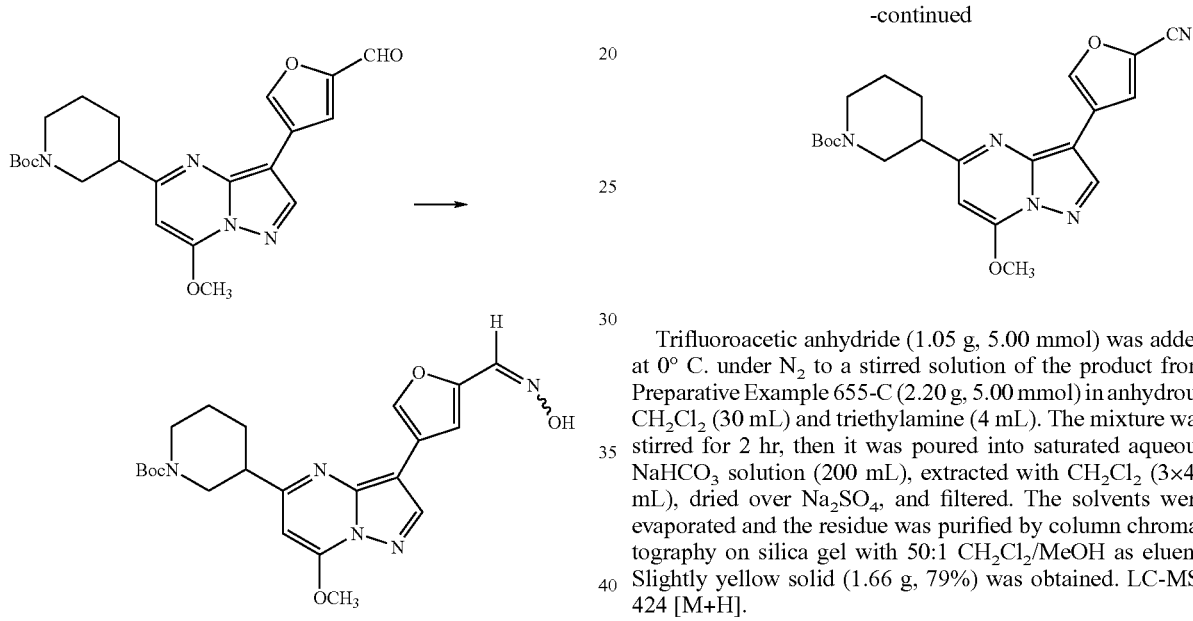 | | LCMS: MH+ = 427 |

Preparative Example 655-C

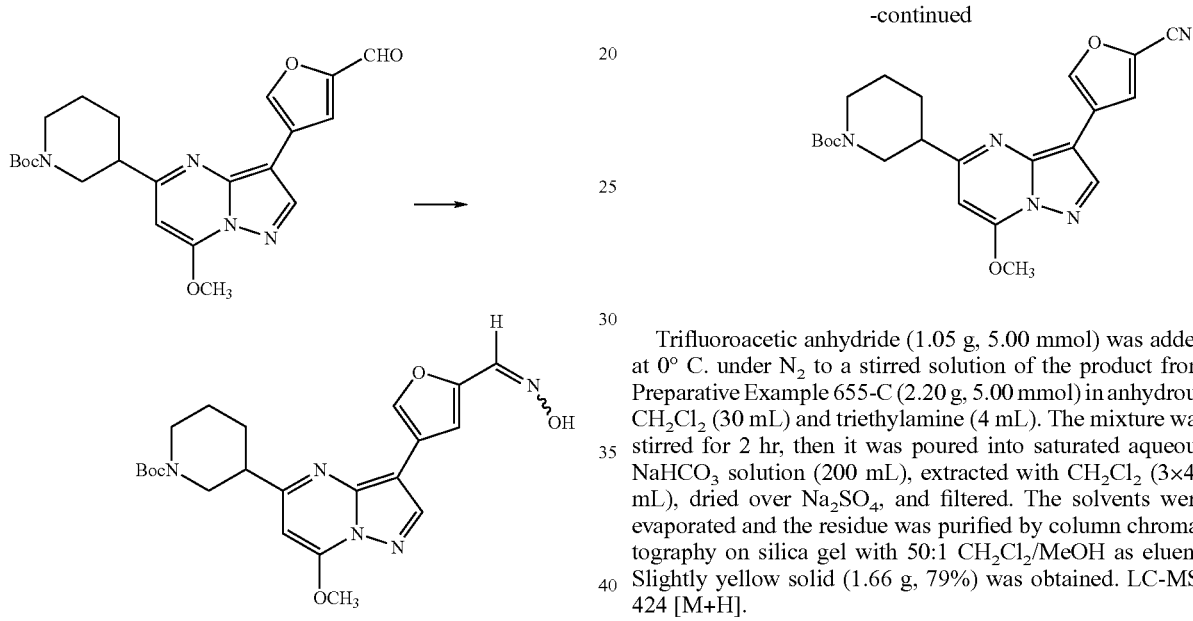

A mixture of the product from Preparative Example 652-C (3.82 g, 9.00 mmol), NH$_2$OH.HCl (750 mg, 10.76 mmol), and triethylamine (4.0 mL) in CH$_2$Cl$_2$ (30 mL) and MeOH (30 mL) was stirred in a closed flask at 25° C. for 3 hr. The solvent was evaporated and the residue was chromatographed on silica gel with 20:1 CH$_2$Cl$_2$/MeOH as eluent. Slightly yellow solid (2.20 g, 56%) was obtained. LC-MS: 442 [M+H].

Preparative Example 656-C

-continued

Trifluoroacetic anhydride (1.05 g, 5.00 mmol) was added at 0° C. under N$_2$ to a stirred solution of the product from Preparative Example 655-C (2.20 g, 5.00 mmol) in anhydrous CH$_2$Cl$_2$ (30 mL) and triethylamine (4 mL). The mixture was stirred for 2 hr, then it was poured into saturated aqueous NaHCO$_3$ solution (200 mL), extracted with CH$_2$Cl$_2$ (3×40 mL), dried over Na$_2$SO$_4$, and filtered. The solvents were evaporated and the residue was purified by column chromatography on silica gel with 50:1 CH$_2$Cl$_2$/MeOH as eluent. Slightly yellow solid (1.66 g, 79%) was obtained. LC-MS: 424 [M+H].

Preparative Example 660-C

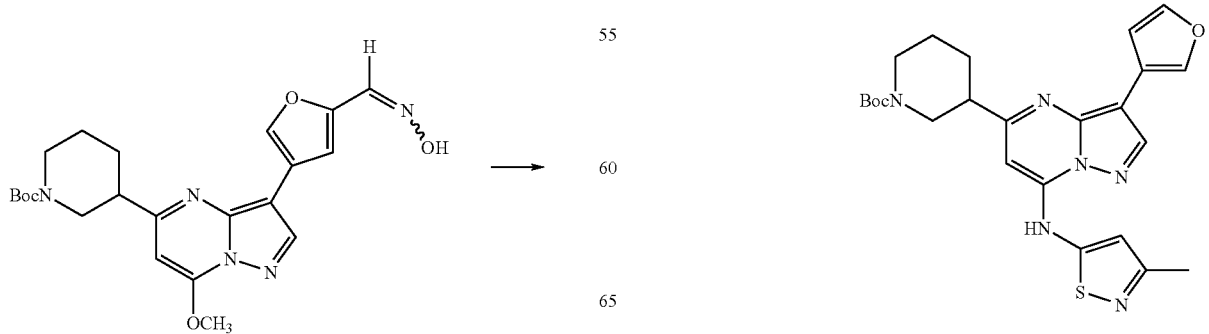

Anhydrous DMSO (2 mL) was added under $N_2$ to a mixture of 5-amino-3-methylisothiazole hydrochloride (58 mg, 0.38 mmol) and 60% NaH (30 mg, 0.76 mmol). The mixture was stirred at 25° C. for 0.5 hr, then a solution of the product from Preparative Example 650-C (170 mg, 0.42 mmol) was added and the resulting mixture was stirred at 25° C. for 18 hr. The mixture was poured into brine (100 mL), extracted with 10:1 EtOAc/$CH_2Cl_2$ mixture (3×30 mL), washed with brine (2×50 mL), dried over $Na_2SO_4$, and filtered. The solvents were evaporated and the residue was purified by column chromatography on silica gel with 20:1 $CH_2Cl_2$/MeOH as eluent. Yellow solid (74 mg, 48%) was obtained. LC-MS: 481 [M+H].

Preparative Example 661-C and 662-C

By essentially same procedure set forth in Preparative Example 660-C, only using different starting materials given in Column 1, compounds given in Column 2 of Table 110-C were prepared.

Example 500-C

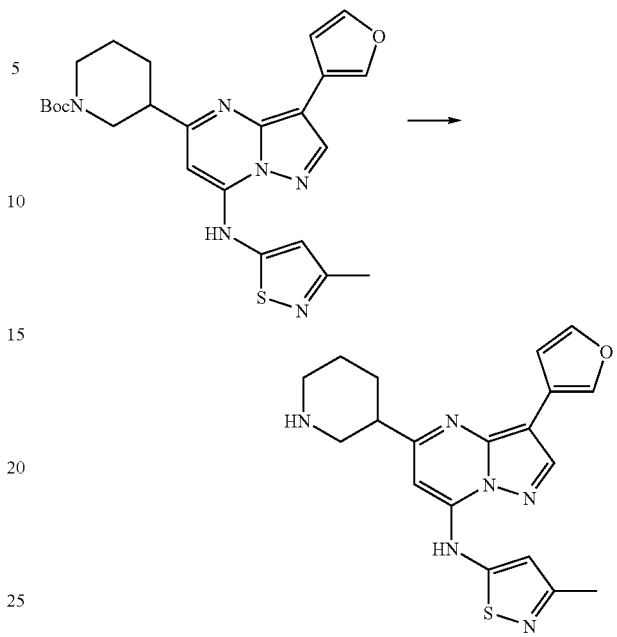

TABLE 110-C

| Prep. Ex. | Column 1 | Column 2 | Data |
|---|---|---|---|
| 661-C | | | LCMS: $MH^+$ = 517 |
| 662-C | | | LCMS: $MH^+$ = 506 |

A mixture of the product from Preparative Example 660-C (74 mg) in TFA (21 mL) and H₂O (2 mL) was stirred at 25° C. under N₂ for 5 hr. The solvents were evaporated, to the residue was added NaHCO₃ (200 mg) and 6:1 CH₂Cl₂/MeOH (1 mL), and the mixture was stirred at 25° C. under N₂ for 0.5 hr. The mixture was loaded onto a column and was purified by column chromatography on silica gel with 4:1 CH₂Cl₂/7N NH₃ in MeOH as eluent. Pale yellow solid (30 mg, 51%) was obtained. LC-MS: 381 [M+H]. Mp=115-118° C.

Example 510-C-530-C

By essentially same procedure set forth in Example 500-C, only using different starting materials given in Column 1, compounds given in Column 2 of Table 120-C were prepared.

TABLE 120-C

| Ex. | Column 1 | Column 2 | Data |
|---|---|---|---|
| 510-C | | | LCMS: MH⁺ = 417 wax |
| 520-C | | | LCMS: MH⁺ = 406 waxy solid |
| 530-C | | | LCMS: MH⁺ = 424 waxy solid |

Example 540-C and 550-C

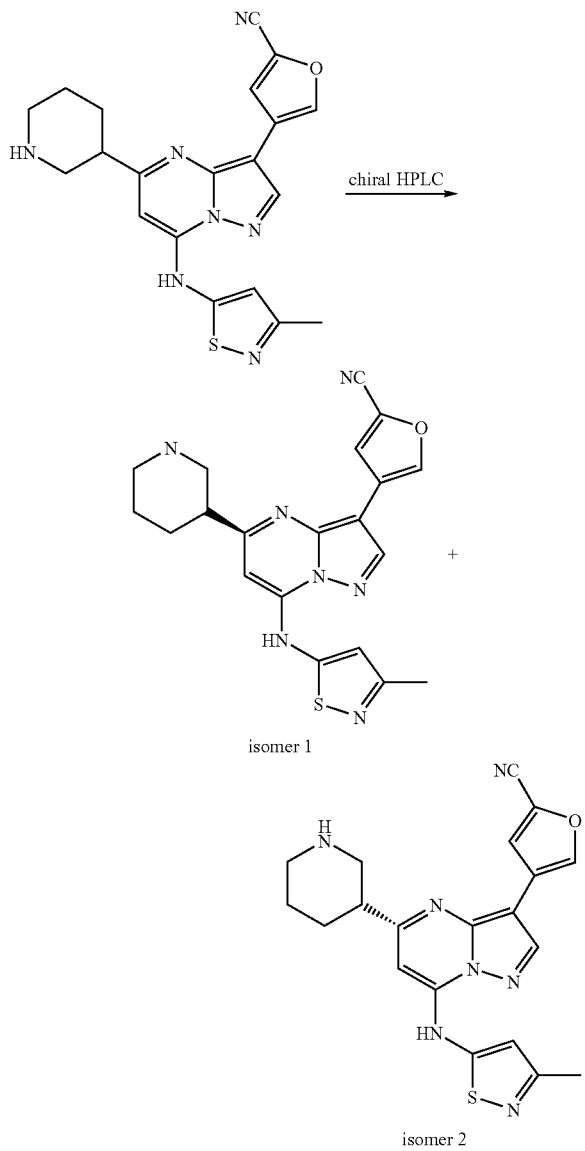

20 mg of the product from Example 520-C was dissolved in warm 2-propanol (3 mL), the solution was allowed to cool to 25° C., hexane (1 mL) was added, the solution was filtered and the filtrate was injected on a semipreparative Chiralcel AD column. Chromatography with mobile phase 75:25 hexane/2-propanol with 0.2% diethylamine afforded two isomers: fast eluting (isomer 1): 5 mg, pale yellow solid; LC-MS: 406 [M+H]; Mp=188-190° C. and slow eluting (isomer 2): 5 mg, pale yellow solid; LC-MS: 406 [M+H]; Mp=187-190° C.

ASSAY: The assay on the compounds of the present invention may be performed as follows.

BACULOVIRUS CONSTRUCTIONS: Cyclin E is cloned into pVL1393 (Pharmingen, La Jolla, Calif.) by PCR, with the addition of 5 histidine residues at the amino-terminal end to allow purification on nickel resin. The expressed protein is approximately 45 kDa. CDK2 is cloned into pVL1393 by PCR, with the addition of a haemaglutinin epitope tag at the carboxy-terminal end (YDVPDYAS). The expressed protein is approximately 34 kDa in size.

ENZYME PRODUCTION: Recombinant baculoviruses expressing cyclin E and CDK2 are co-infected into SF9 cells at an equal multiplicity of infection (MOI=5), for 48 hrs. Cells are harvested by centrifugation at 1000 RPM for 10 minutes, then pellets lysed on ice for 30 minutes in five times the pellet volume of lysis buffer containing 50 mM Tris pH 8.0, 150 mM NaCl, 1% NP40, 1 mM DTT and protease inhibitors (Roche Diagnostics GmbH, Mannheim, Germany). Lysates are spun down at 15000 RPM for 10 minutes and the supernatant retained. 5 ml of nickel beads (for one liter of SF9 cells) are washed three times in lysis buffer (Qiagen GmbH, Germany). Imidazole is added to the baculovirus supernatant to a final concentration of 20 mM, then incubated with the nickel beads for 45 minutes at 4° C. Proteins are eluted with lysis buffer containing 250 mM imidazole. Eluate is dialyzed overnight in 2 liters of kinase buffer containing 50 mM Tris pH 8.0, 1 mM DTT, 10 mM MgCl2, 100 uM sodium orthovanadate and 20% glycerol. Enzyme is stored in aliquots at −70° C.

IN VITRO KINASE ASSAY: Cyclin E/CDK2 kinase assays are performed in low protein binding 96-well plates (Corning Inc, Corning, N.Y.). Enzyme is diluted to a final concentration of 50 μg/ml in kinase buffer containing 50 mM Tris pH 8.0, 10 mM MgCl$_2$, 1 mM DTT, and 0.1 mM sodium orthovanadate. The substrate used in these reactions is a biotinylated peptide derived from Histone H1 (from Amersham, UK). The substrate is thawed on ice and diluted to 2 μM in kinase buffer. Compounds are diluted in 10% DMSO to desirable concentrations. For each kinase reaction, 20 μl of the 50 μg/ml enzyme solution (1 μg of enzyme) and 20 μl of the 2 μM substrate solution are mixed, then combined with 10 μl of diluted compound in each well for testing. The kinase reaction is started by addition of 50 μl of 2 μM ATP and 0.1 μCi of 33P-ATP (from Amersham, UK). The reaction is allowed to run for 1 hour at room temperature. The reaction is stopped by adding 200 μl of stop buffer containing 0.1% Triton X-100, 1 mM ATP, 5 mM EDTA, and 5 mg/ml streptavidine coated SPA beads (from Amersham, UK) for 15 minutes. The SPA beads are then captured onto a 96-well GF/B filter plate (Packard/Perkin Elmer Life Sciences) using a Filtermate universal harvester (Packard/Perkin Elmer Life Sciences.). Non-specific signals are eliminated by washing the beads twice with 2M NaCl then twice with 2 M NaCl with 1% phosphoric acid. The radioactive signal is then measured using a Top-Count 96 well liquid scintillation counter (from Packard/Perkin Elmer Life Sciences).

IC$_{50}$ DETERMINATION: Dose-response curves are plotted from inhibition data generated, each in duplicate, from 8 point serial dilutions of inhibitory compounds. Concentration of compound is plotted against % kinase activity, calculated by CPM of treated samples divided by CPM of untreated samples. To generate IC$_{50}$ values, the dose-response curves are then fitted to a standard sigmoidal curve and IC$_{50}$ values are derived by nonlinear regression analysis. The IC50 values for certain non-limiting, illustrative compounds of the invention are provided in Table 2.

TABLE 2

| CMPD | IC50 (μM) |
|---|---|
| (structure) | 46 |
| (structure) | 3.3 |
| (structure) | 40 |
| (structure) | 0.076 |

TABLE 2-continued

| CMPD | IC50 (μM) |
|---|---|
| (structure) | 3.6 |
| (structure) | 0.05 |
| (structure) | 49 |
| (structure) | 6.7 |

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.
What is claimed is:
1. A compound selected from the group consisting of the compounds of the formula:
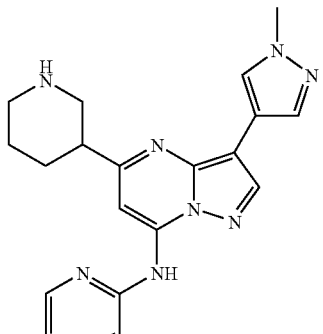
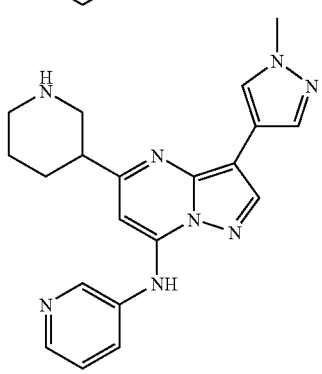
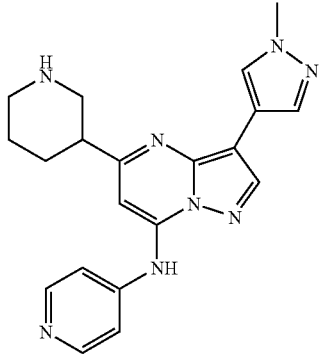
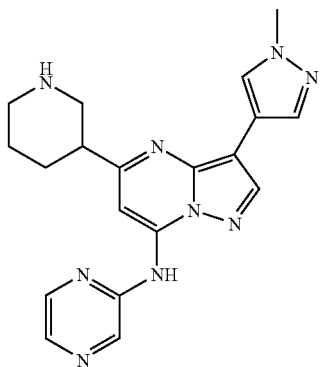
-continued
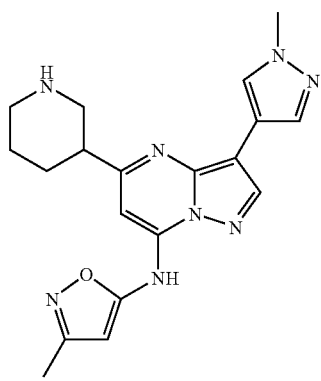
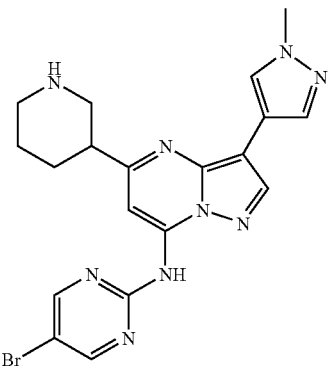
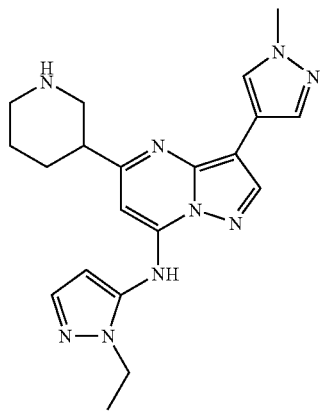
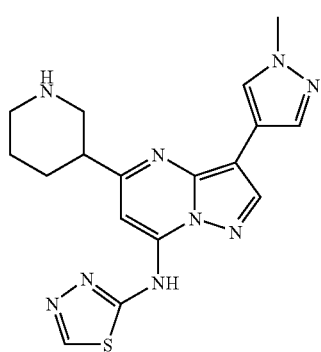

-continued
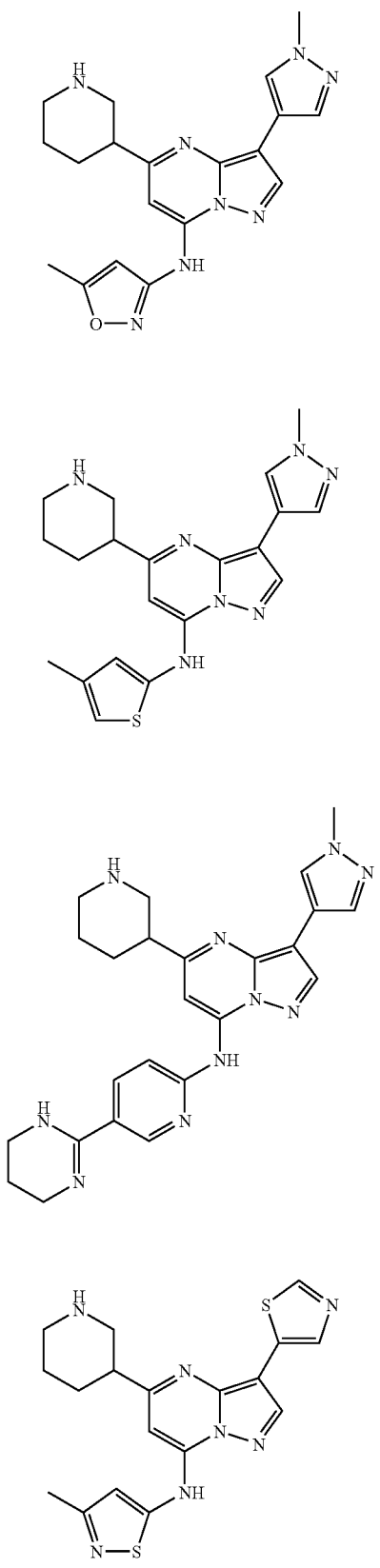
-continued
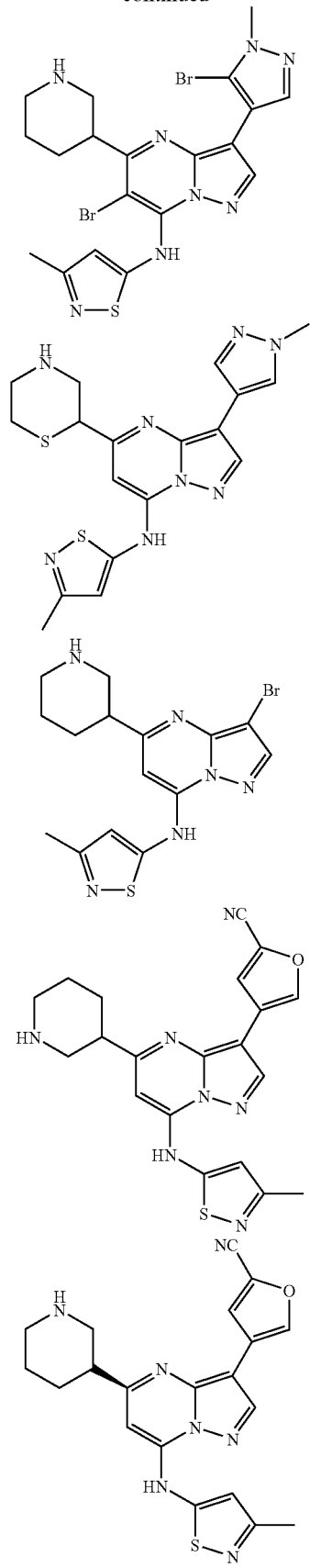

-continued
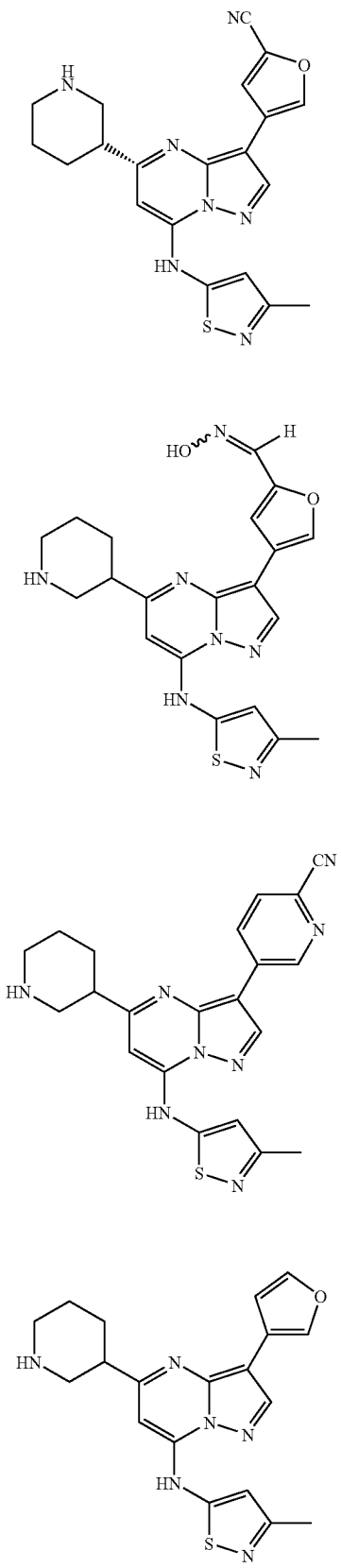
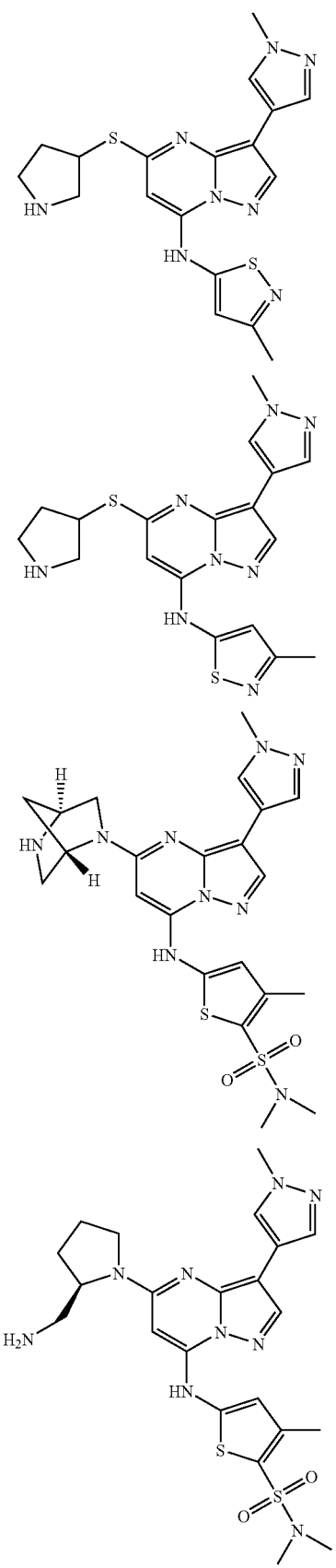

-continued
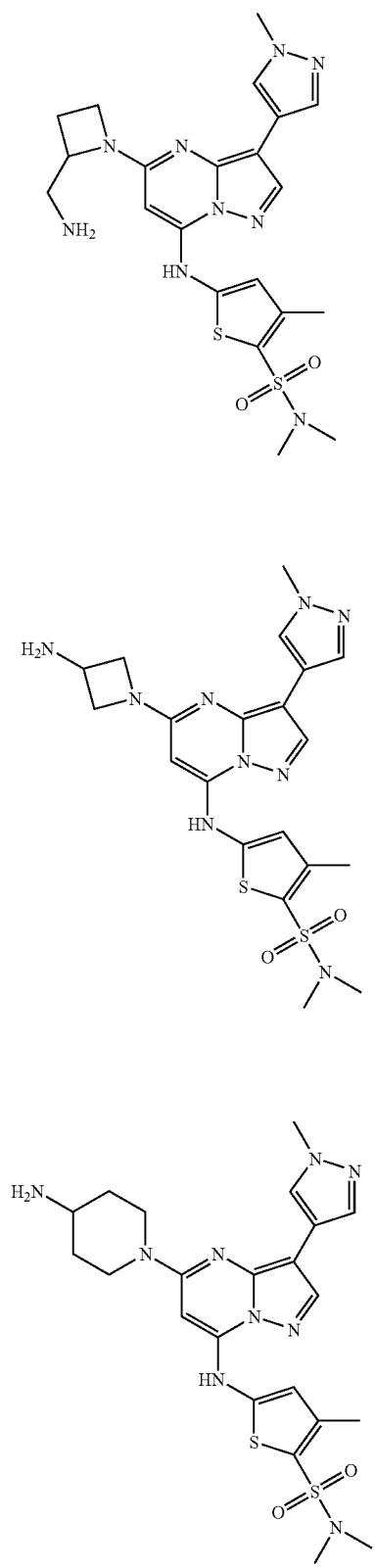
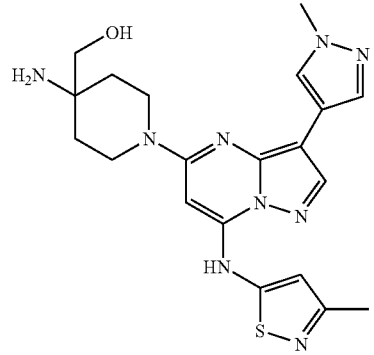
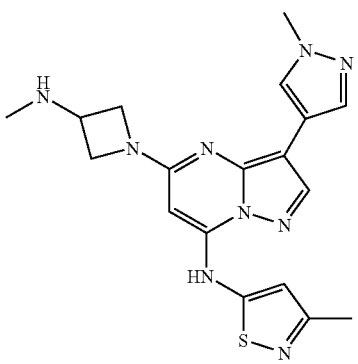
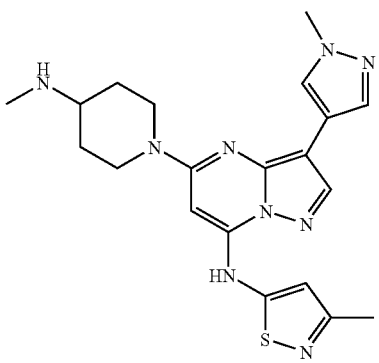
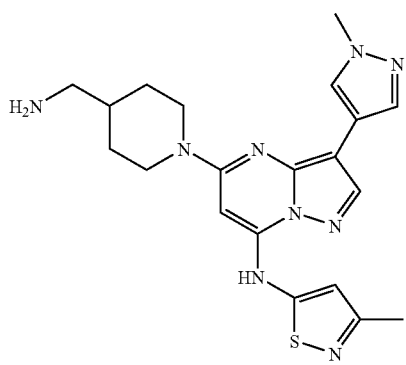

101
-continued
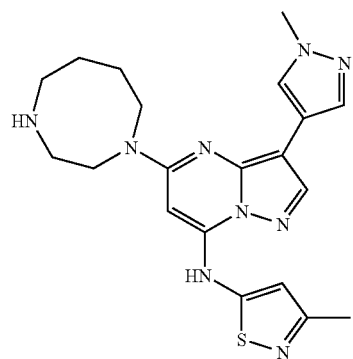
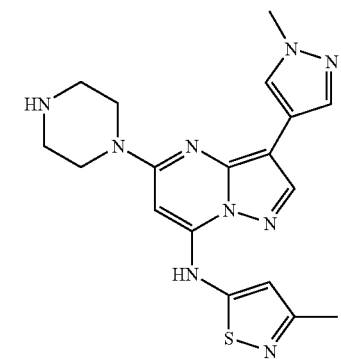
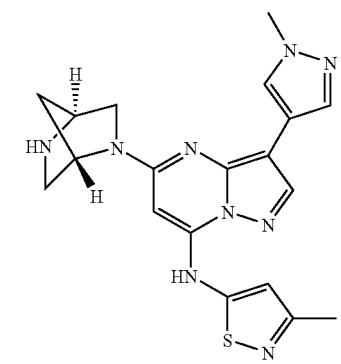
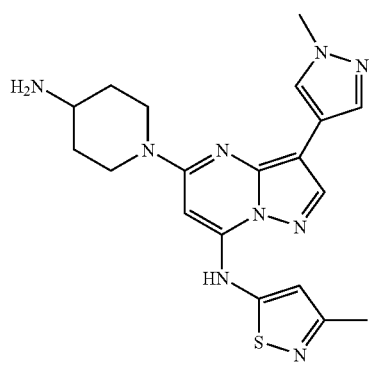
102
-continued
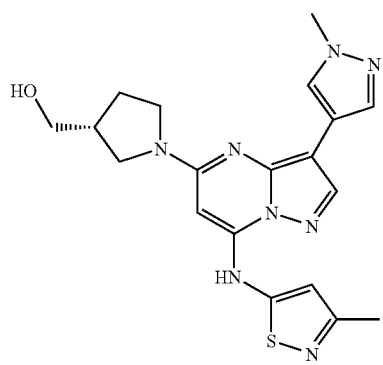
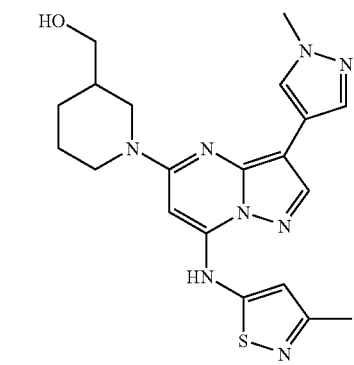
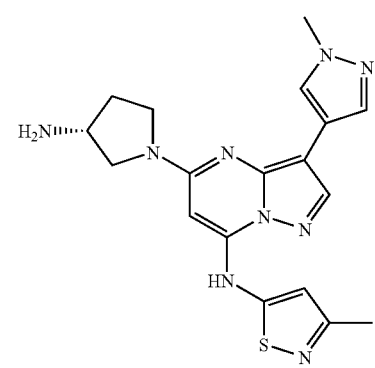
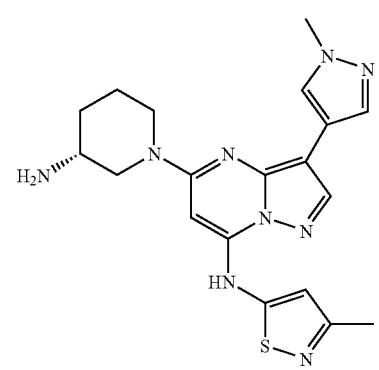

-continued
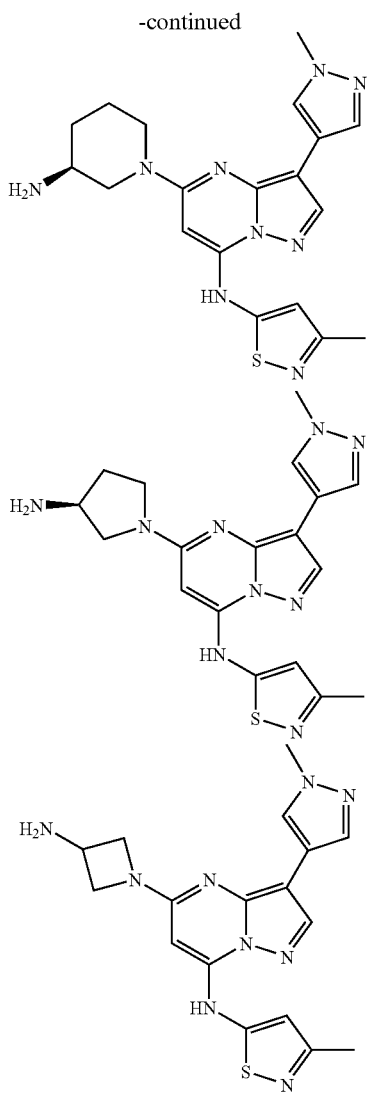
-continued
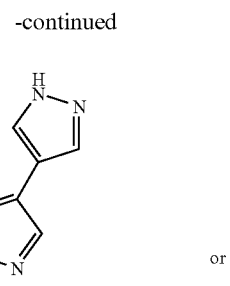
or
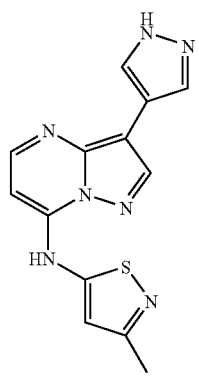
or a pharmaceutically acceptable salt thereof.
2. A pharmaceutical composition comprising an amount of at least one compound of claim 1, or a pharmaceutically acceptable salt thereof, in combination with at least one pharmaceutically acceptable carrier.
3. A compound of claim 1 in isolated and purified form.
* * * * *